United States Patent
Onobori et al.

(10) Patent No.: US 10,610,091 B2
(45) Date of Patent: Apr. 7, 2020

(54) ENDOSCOPE LIGHT SOURCE DEVICE AND ENDOSCOPE SYSTEM

(71) Applicant: HOYA CORPORATION, Tokyo (JP)

(72) Inventors: Kunihiko Onobori, Tokyo (JP); Masaaki Fukuda, Tokyo (JP)

(73) Assignee: HOYA CORPORATION, Tokyo (JP)

(*) Notice: Subject to any disclaimer, the term of this patent is extended or adjusted under 35 U.S.C. 154(b) by 0 days.

(21) Appl. No.: 15/999,500

(22) PCT Filed: Feb. 20, 2017

(86) PCT No.: PCT/JP2017/006124
§ 371 (c)(1),
(2) Date: Aug. 17, 2018

(87) PCT Pub. No.: WO2017/142097
PCT Pub. Date: Aug. 24, 2017

(65) Prior Publication Data
US 2019/0110672 A1    Apr. 18, 2019

Related U.S. Application Data

(63) Continuation of application No. PCT/JP2016/054812, filed on Feb. 19, 2016.

(51) Int. Cl.
*G02B 21/06* (2006.01)
*A61B 1/06* (2006.01)
(Continued)

(52) U.S. Cl.
CPC .......... *A61B 1/0676* (2013.01); *A61B 1/0638* (2013.01); *A61B 1/0653* (2013.01);
(Continued)

(58) Field of Classification Search
CPC ... A61B 1/0638; A61B 1/0684; A61B 1/0653; A61B 1/07
See application file for complete search history.

(56) References Cited

U.S. PATENT DOCUMENTS 9,025,244 B2 * 5/2015 Reimer .................. A61B 1/043
359/368
2009/0167149 A1 * 7/2009 Ito ........................ A61B 1/0638
313/501
(Continued)

FOREIGN PATENT DOCUMENTS

JP    2012105715 A    6/2012
JP    2012170488 A    10/2012
(Continued)

OTHER PUBLICATIONS

PCT/JP2017/006124, "International Search Report", dated Apr. 11, 2017, 4 pages.

*Primary Examiner* — Andrew J Coughlin
(74) *Attorney, Agent, or Firm* — Kilpatrick Townsend & Stockton LLP

(57) ABSTRACT

An endoscope light source device is constituted by a first light source unit that emits light in a first wavelength band, a second light source unit that emits light in a second wavelength band, a light path combining means for combining the light paths of the light emitted from the first and second light source units, and a light source control means for controlling light emission of the light source units separately. When the light source units are driven to emit light in a first mode, the respective wavelength bands of light are emitted at a first intensity ratio and combined with each other to obtain normal light, which is supplied to an endoscope. Also, when the light source units are driven to emit light in a second mode, the respective wavelength bands of light are emitted at a second intensity ratio having a relatively lower ratio of the light in the second wavelength band, and are combined with each other to obtain special light that has a high light absorption rate in a specific biological tissue, and the special light is supplied to the endoscope.

20 Claims, 10 Drawing Sheets

(51) Int. Cl.
  *A61B 1/04* (2006.01)
  *G02B 23/24* (2006.01)
(52) U.S. Cl.
  CPC .............. *A61B 1/0684* (2013.01); *A61B 1/04* (2013.01); *G02B 23/2423* (2013.01)

(56) References Cited

U.S. PATENT DOCUMENTS

| | | | |
|---|---|---|---|
| 2011/0237894 A1* | 9/2011 | Ozawa | A61B 1/043 600/168 |
| 2012/0265041 A1 | 10/2012 | Yamaguchi et al. | |
| 2013/0053646 A1 | 2/2013 | Yamamoto | |
| 2013/0148345 A1 | 6/2013 | Yabe | |
| 2014/0107421 A1 | 4/2014 | Nakatate et al. | |
| 2015/0327755 A1 | 11/2015 | Daidoji et al. | |
| 2015/0374218 A1 | 12/2015 | Nishio et al. | |

FOREIGN PATENT DOCUMENTS

| | | | |
|---|---|---|---|
| JP | 2012228503 A | 11/2012 | |
| JP | 2013046688 A | 3/2013 | |
| JP | 2013252357 A | 12/2013 | |
| JP | 2014144144 A | 8/2014 | |
| JP | 2014171511 A | 9/2014 | |
| JP | 2015183085 A | 10/2015 | |
| JP | 6053079 B2 | 12/2016 | |
| JP | 6298518 B2 | 3/2018 | |
| JP | 6417014 B2 | 10/2018 | |
| WO | 2012108420 A | 8/2012 | |

* cited by examiner (a)

(b)

ENDOSCOPE LIGHT SOURCE DEVICE AND ENDOSCOPE SYSTEM

TECHNICAL FIELD

The present disclosure relates to an endoscope light source device and an endoscope system for irradiating a subject with light.

BACKGROUND ART

An endoscope system that can capture special images by changing the spectral intensity characteristics of irradiation light is known. A specific configuration of a light source device used in this type of endoscope system is disclosed in WO 2012/108420 (called "Patent Document 1" hereinafter), for example.

The endoscope system described in Patent Document 1 includes a light source device that is provided with two light emitting diodes (LEDs) and an optical filter. One of the two LEDs is a purple LED that emits light in the purple wavelength band. Also, the other LED is a fluorescent LED that has a blue LED and a yellow phosphor, and emits pseudo white light by mixing the blue LED and the yellow fluorescent light. The optical filter is a wavelength selection filter that allows only light in a specific wavelength region to pass, and can be inserted into and removed from the light path of irradiation light emitted from the fluorescent LED.

With the light source device described in Patent Document 1, when the optical filter has been removed from the light path, a subject is irradiated with light emitted from the fluorescent LED as white light, with no limitation of the wavelength band. However, when the optical filter is inserted into the light path, the wavelength band of the irradiation light emitted from the fluorescent LED is limited, and the subject is irradiated with both this irradiation light and the irradiation light emitted from the purple LED. In this way, by changing the spectral intensity characteristics of the irradiation light and irradiating the subject with only light in a specific wavelength band, it is possible to obtain a captured image in which a specific tissue inside the subject's body is emphasized.

Summary of Disclosure

With the light source device described in Patent Document 1, in order to obtain irradiation light that has a high intensity in only a specific wavelength band, the wavelength band of the light emitted from the fluorescent LED is limited by the optical filter, thus cutting out light in unnecessary wavelength bands. The subject is not irradiated with this light that has been cut out, thus causing the problem that the light use efficiency of the light source device is low. Also, because the optical filter allows substantially only light in a specific wavelength band to pass, there is a problem that the intensity of the light that passes through the optical filter is low, and a bright captured image cannot be obtained.

The present disclosure was achieved in light of the above-described circumstances, and an aspect of the present disclosure is to provide an endoscope light source device and an endoscope system in which irradiation light having a high intensity in only a specific wavelength band can be emitted with a high light use efficiency.

An endoscope light source device according to an embodiment of the present disclosure includes: a first light source unit that emits light in a first wavelength band; a second light source unit that emits light in a second wavelength band having a peak wavelength that is different from a peak wavelength of the first wavelength band; a first light path combining means for combining a light path of the light emitted from the first light source unit and a light path of the light emitted from the second light source unit; and a light source control means for controlling light emission of the first light source unit and the second light source unit separately in accordance with a plurality of modes. In this configuration, when the first light source unit and the second light source unit are driven by the light source control means to emit light in a first mode, the light in the first wavelength band and the light in the second wavelength band are emitted at a first intensity ratio and combined by the first light path combining means to obtain normal light that has a wide wavelength range in a visible light region, and the normal light is supplied to an endoscope, and when the first light source unit and the second light source unit are driven by the light source control means to emit light in a second mode, the light in the first wavelength band and the light in the second wavelength band are emitted at a second intensity ratio having a relatively lower ratio of the light in the second wavelength band than the first intensity ratio, and are combined by the first light path combining means to obtain special light that has a high light absorption rate in a specific biological tissue, and the special light is supplied to the endoscope.

According to this configuration, by separately driving the first light source unit and the second light source unit to emit light, the irradiation light for irradiation of a subject can be switched between normal light, which has a wide wavelength range in the visible light region, and special light, in which the light in the wavelength band having a high light absorption rate in a specific biological tissue in the subject has a higher intensity than the light in other wavelength bands. Also, when switching the spectral intensity characteristics of the irradiation light, there is no need to use an optical filter such as a wavelength limiting filter, thus making it possible to suppress a loss of light that accompanies the switching of the spectral intensity characteristics.

Also, in an embodiment of the present disclosure, the endoscope light source device further includes: a third light source unit that emits light in a third wavelength band having a peak wavelength that is different from the peak wavelength of the first wavelength band and the peak wavelength of the second wavelength band; and a second light path combining means for combining a light path of light combined by the first light path combining means and a light path of the light emitted from the third light source unit, for example. In this configuration, in the first mode, the light source control means causes the third light source unit to emit light at a predetermined intensity ratio with respect to the first light source unit and the second light source unit, and in the second mode, the light source control means does not cause the third light source unit to emit light.

Also, in an embodiment of the present disclosure, the endoscope light source device further includes: a fourth light source unit that emits light in a fourth wavelength band having a peak wavelength that is different from the peak wavelength of the first wavelength band, the peak wavelength of the second wavelength band, and the peak wavelength of the third wavelength band; and a third light path combining means for combining a light path of light combined by the second light path combining means and a light path of the light emitted from the fourth light source unit, for example. In this configuration, in the first mode, the light source control means causes the fourth light source unit to emit light at a predetermined intensity ratio with respect to the first light source unit, the second light source unit, and the third light source unit, and in the second mode, the light source control means does not cause the fourth light source unit to emit light.

Also, in an embodiment of the present disclosure, the first light source unit has a first solid-state light emitting element, and a first phosphor that is excited by light emitted from the first solid-state light emitting element and emits light, for example.

Also, in an embodiment of the present disclosure, the second light source unit has a second solid-state light emitting element, and a second phosphor that is excited by light emitted from the second solid-state light emitting element and emits light, for example.

Also, in an embodiment of the present disclosure, the second phosphor includes two phosphors that are excited by the light emitted from the second solid-state light emitting element and emit light having mutually different peak wavelengths, for example.

Also, in an embodiment of the present disclosure, the first solid-state light emitting element emits light in a purple wavelength band, and the first phosphor is a phosphor that emits fluorescent light in a blue wavelength band, for example. In this case, in the light emitted from the first light source unit, an intensity of the fluorescent light in the blue wavelength band is weaker than an intensity of the light in the purple wavelength band, for example.

Also, an endoscope system according to an embodiment of the present disclosure includes any of the endoscope light source devices described above, and an endoscope.

According to an embodiment of the present disclosure, an endoscope light source device and an endoscope system are provided in which irradiation light having a high intensity in only a specific wavelength band can be emitted with a high light use efficiency.

DESCRIPTION OF EMBODIMENTS

Hereinafter, embodiments of the present disclosure will be described with reference to the drawings. Note that an electronic endoscope system that includes an endoscope light source device is taken as an example of an embodiment of the present disclosure in the following description.

First Embodiment

Figure 1:
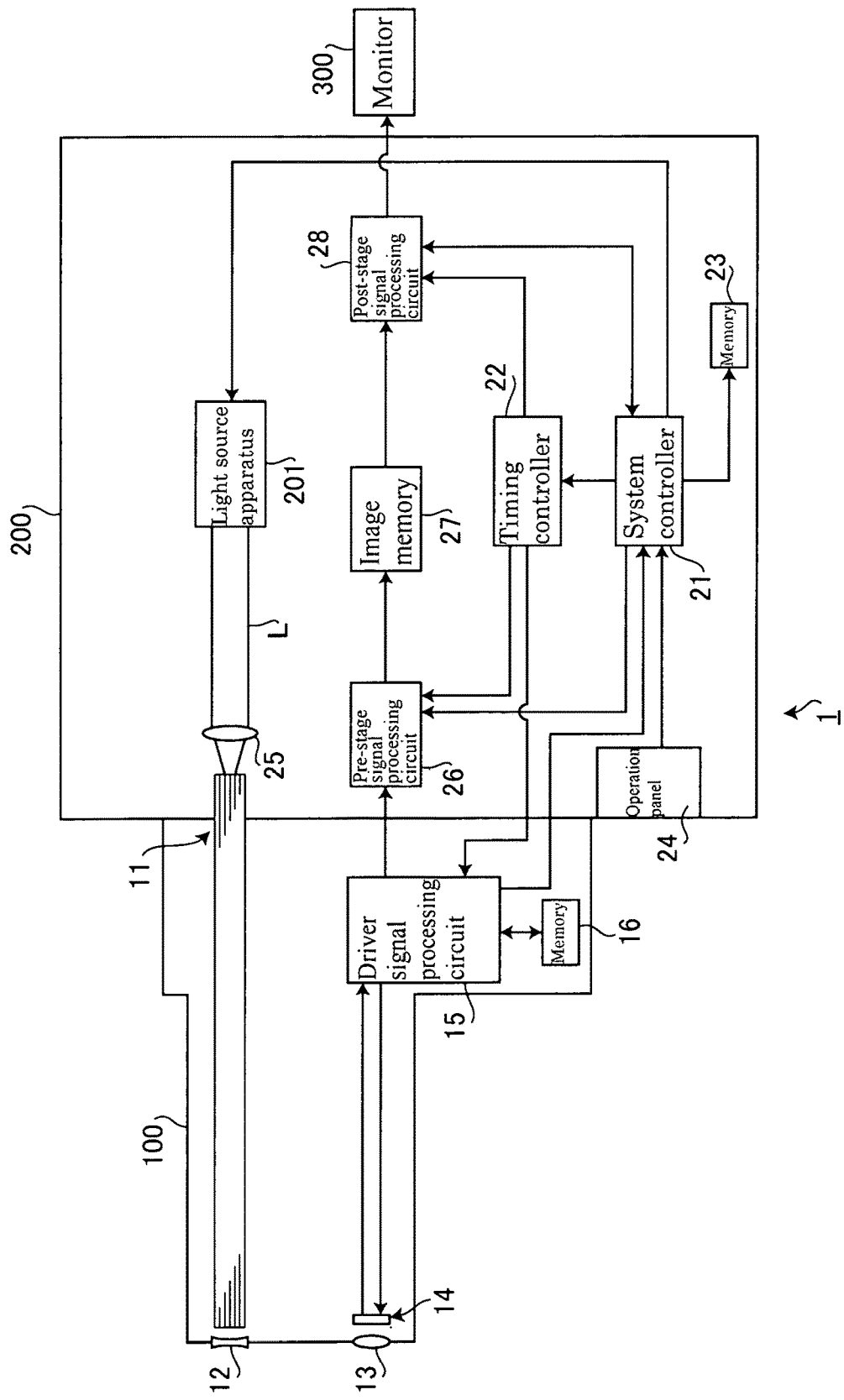
FIG. 1 is a block diagram showing a configuration of an electronic endoscope system according to a first embodiment of the present disclosure.

FIG. 1 is a block diagram showing the configuration of an electronic endoscope system 1 that includes an endoscope light source device 201 according to a first embodiment of the present disclosure. As shown in FIG. 1, the electronic endoscope system 1 is a system specialized for medical use, and includes an electronic endoscope 100, a processor 200, and a monitor 300.

The processor 200 includes a system controller 21 and a timing controller 22. The system controller 21 executes various programs stored in a memory 23 and performs overall control of the electronic endoscope system 1. Also, the system controller 21 is connected to an operation panel 24. The system controller 21 changes operations of the electronic endoscope system 1 and parameters for various operations in accordance with instructions from an operator that are input using the operation panel 24. One example of an instruction input by an operator is an instruction for switching the observation mode of the electronic endoscope system 1. Examples of observation modes include a normal observation mode and a special observation mode. The observation modes will be described in detail later. The timing controller 22 outputs a clock pulse, which is for adjustment of the timing of the operations of portions, to circuits in the electronic endoscope system 1.

Figure 2:
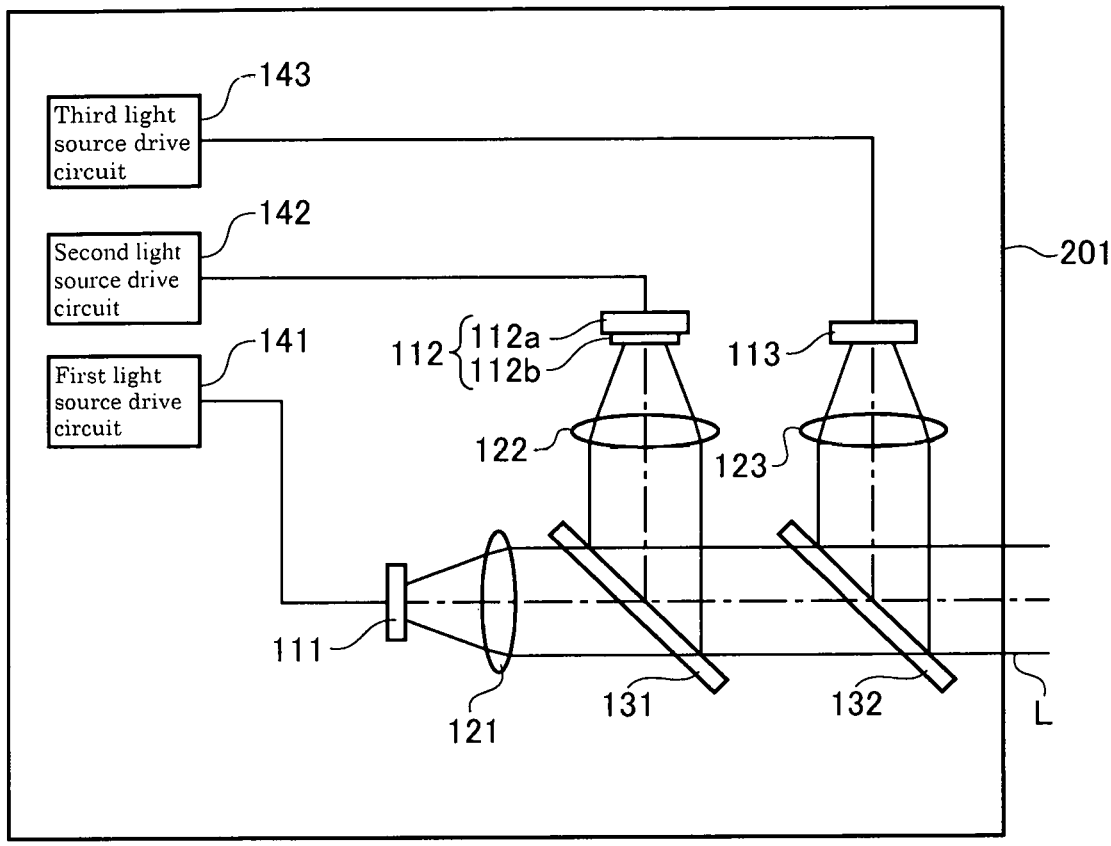
FIG. 2 is a block diagram showing a configuration of an endoscope light source device according to the first embodiment of the present disclosure.

The processor 200 includes a light source device 201. FIG. 2 shows a block diagram of the light source device 201 according to the first embodiment of the present disclosure. The light source device 201 includes a first light source unit 111, a second light source unit 112, and a third light source unit 113. The emission of light by the first to third light source units 111 to 113 is controlled by first to third light source drive circuits 141 to 143 respectively.

Although the light source device 201 is provided in the processor 200 in the present embodiment, in another embodiment the light source device 201 may be a device that is separate from the processor 200 (or more accurately a portion that constitutes an image processing device).

The first light source unit 111 is a purple light emitting diode (LED) that emits light in the purple wavelength band (e.g., wavelengths of 395 to 435 nm). The second light source unit 112 has a blue LED 112a that emits light in the blue wavelength band (e.g., wavelengths of 425 to 455 nm) and a green phosphor 112b. The green phosphor 112b is excited by blue LED light emitted from the blue LED 112a and emits fluorescent light in the green wavelength band (e.g., wavelengths of 460 to 600 nm). The third light source unit 113 is a red light emitting diode (LED) that emits light in the red wavelength band (e.g., wavelengths of 630 to 670 nm).

Collimator lenses 121 to 123 are arranged in front of, with respect to the light emission direction, the light source units 111 to 113 respectively. The purple LED light emitted from the first light source unit 111 is converted into parallel light by the collimator lens 121 and is then incident on a dichroic mirror 131. Also, the light emitted from the second light source unit 112, that is to say blue LED light and green fluorescent light, is converted into parallel light by the collimator lens 122 and is then incident on the dichroic mirror 131. The dichroic mirror 131 combines the light path of the light emitted from the first light source unit 111 and the light path of the light emitted from the second light source unit 112. Specifically, the dichroic mirror 131 has a cutoff wavelength of approximately 430 nm, and has a characteristic of allowing the passage of light with a shorter wavelength than the cutoff wavelength and reflecting light with a wavelength greater than or equal to the cutoff wavelength. For this reason, the purple LED light emitted from the first light source unit 111 passes through the dichroic mirror 131, and the green fluorescent light emitted from the second light source unit 112 is reflected by the dichroic mirror 131. Accordingly, the light paths of the purple LED light and the green fluorescent light are combined with each other. The light on the light paths combined by the dichroic mirror 131 is incident on a dichroic mirror 132.

Also, the red LED light emitted from the third light source unit 113 is converted into parallel light by the collimator lens 123 and is then incident on the dichroic mirror 132. The dichroic mirror 132 combines the light path of light from the dichroic mirror 131 and the light path of light emitted from the third light source unit 113. Specifically, the dichroic mirror 132 has a cutoff wavelength of approximately 620 nm, and has a characteristic of allowing the passage of light with a shorter wavelength than the cutoff wavelength and reflecting light with a wavelength greater than or equal to the cutoff wavelength. For this reason, the light path of the purple LED light and the green fluorescent light from the dichroic mirror 131 and the light path of the red LED light emitted from the third light source unit 113 are combined by the dichroic mirror 132, and the light on the combined light paths is emitted from the light source device 201 as irradiation light L.

Figure 3:
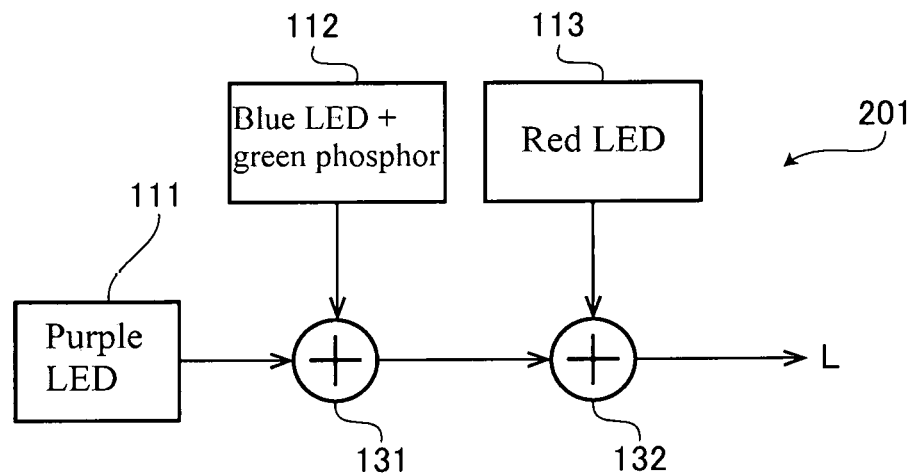
FIG. 3 is a block diagram of the endoscope light source device according to the first embodiment of the present disclosure.

FIG. 3 is a block diagram that conceptually shows only the light source units 111 to 113 and the dichroic mirrors 131 and 132 in the light source device 201. The green phosphor 112b of the second light source unit 112 is attached to the light emitting surface of the blue LED 112a and is constituted as a single body with the blue LED 112a, and therefore the green phosphor 112b and the blue LED 112a are shown as one block in FIG. 3.

Also, the dichroic mirrors 131 and 132 each combine the light paths of light that has different wavelengths. For this reason, in FIG. 3, the dichroic mirrors 131 and 132 are each denoted by the addition sign "+". Also, FIG. 3 does not show the collimator lenses 121 to 123 that are arranged in front of the light source units 111 to 113.

The arrows in FIG. 3 denote the light paths of light. In the example shown in FIG. 3, the light path of the purple LED light emitted from the first light source unit 111 and the light path of the blue LED light and the green fluorescent light emitted from the second light source unit 112 are combined by the dichroic mirror 131. The combined light path of the light obtained by the dichroic mirror 131 and the light path of the red LED light emitted from the third light source unit 113 are combined by the dichroic mirror 132. The light path of the light combined by the dichroic mirror 132 is emitted from the light source device 201 as the irradiation light L.

The irradiation light L emitted from the light source device 201 is condensed on the entrance surface of an LCB (Light Carrying Bundle) 11 by a condensing lens 25, and enters the LCB 11.

The irradiation light L that entered the LCB 11 propagates inside the LCB 11. The irradiation light L that propagated inside the LCB 11 exits from the exit surface of the LCB 11 arranged at the distal end of the electronic endoscope 100 and passes through a light distribution lens 12, and then the subject is irradiated with the irradiation light L. Returning light from the subject, which was irradiated by the irradiation light L from the light distribution lens 12, passes through an objective lens 13 and forms an optical image on the light receiving surface of a solid-state image sensor 14.

The solid-state image sensor 14 is a single-plate color CCD (Charge Coupled Device) image sensor that has a Bayer pixel arrangement. The solid-state image sensor 14 accumulates charge according to the light quantity of an optical image formed on pixels on the light receiving surface, generates R (Red), G (Green), and B (Blue) image signals, and outputs the image signals. Note that the solid-state image sensor 14 is not limited to being a CCD image sensor, and may be replaced with a CMOS (Complementary Metal Oxide Semiconductor) image sensor or another type of imaging device. The solid-state image sensor 14 may be an element that includes a complementary color filter.

A driver signal processing circuit 15 is provided in the connection portion of the electronic endoscope 100. An image signal regarding the subject, which was irradiated by light from the light distribution lens 12, is input from the solid-state image sensor 14 to the driver signal processing circuit 15 at a frame cycle. The frame cycle is 1/30 sec, for example. The image signal received from the solid-state image sensor 14 is subjected to predetermined processing by the driver signal processing circuit 15 and output to a pre-stage signal processing circuit 26 of the processor 200.

The driver signal processing circuit 15 also accesses a memory 16 and reads out unique information regarding the electronic endoscope 100. The unique information regarding the electronic endoscope 100 recorded in the memory 16 includes, for example, the pixel count, sensitivity, operable frame rate, and model number of the solid-state image sensor 14. The unique information read out from the memory 16 is output by the driver signal processing circuit 15 to the system controller 21.

The system controller 21 generates control signals by performing various computation based on the unique information regarding the electronic endoscope 100. The system controller 21 uses the generated control signals to control the operations of and the timing of various circuits in the processor 200 so as to perform processing suited to the electronic endoscope that is connected to the processor 200.

A timing controller 22 supplies a clock pulse to the driver signal processing circuit 15 in accordance with timing control performed by the system controller 21. In accordance with the clock pulse supplied from the timing controller 22, the driver signal processing circuit 15 controls the driving of the solid-state image sensor 14 according to a timing synchronized with the frame rate of the images processed by the processor 200.

The pre-stage signal processing circuit 26 performs predetermined signal processing such as demosaicing processing, matrix computation, and Y/C separation on the image signal received in one frame cycle from the driver signal processing circuit 15, and outputs the result to an image memory 27.

The image memory 27 buffers image signals received from the pre-stage signal processing circuit 26, and outputs the image signals to a post-stage signal processing circuit 28 in accordance with timing control performed by the timing controller 22.

The post-stage signal processing circuit 28 performs processing on the image signals received from the image memory 27 to generate screen data for monitor display, and converts the generated monitor display screen data into a predetermined video format signal. The converted video format signal is output to the monitor 300. Accordingly, subject images are displayed on the display screen of the monitor 300.

The electronic endoscope system 1 of the present embodiment has multiple observation modes, including a normal observation mode and a special observation mode. The observation mode is manually or automatically switched according to the subject that is observed. For example, in the case of observing a subject irradiated with normal light, the observation mode is switched to the normal observation mode. Note that normal light is white light or pseudo white light, for example. White light has a flat spectral intensity distribution in the visible light range. Pseudo white light has a spectral intensity distribution that is not flat, and includes a mixture of colors of light in multiple wavelength bands. In the case of obtaining a captured image in which a specific biological tissue is emphasized by irradiating the subject with special light, for example, the observation mode is switched to the special observation mode.

Note that special light is light in a narrow band having a sharp peak at a specific wavelength, for example, and has a high light absorption rate in a specific biological tissue. Examples of specific light wavelengths include light around 415 nm (e.g., 415±5 nm) having a high light absorption rate in outer-layer blood vessels, light around 550 nm (e.g., 550±5 nm) having a high light absorption rate in middle-layer blood vessels that are deeper than those in the outer layer, and light around 650 nm (e.g., 650±5 nm) having a high light absorption rate in deep-layer blood vessels that are deeper than those in the middle layer. Note that the longer the wavelength of the light is, the deeper the light penetrates into the biological tissue. Accordingly, the narrow band light with wavelengths around 415 nm, 550 nm, and 650 nm reach increasingly deeper regions. The following mainly describes the case where outer-layer blood vessels are the biological tissue that is to be emphasized in the special observation mode.

Blood that contains hemoglobin flows through outer-layer blood vessels. Hemoglobin is known to have a peak light absorption rate around 415 nm and 550 nm wavelengths. For this reason, by irradiating the subject with special light that is suited to emphasizing outer-layer blood vessels (specifically, light having a high intensity around a wavelength of 415 nm, which is the peak light absorption rate of hemoglobin, compared to other wavelength bands), it is possible to obtain a captured image in which outer-layer blood vessels are emphasized. Special light having a high intensity around a wavelength of 550 nm has a relatively high light absorption rate in outer-layer blood vessels as well. In other words, special light having a high intensity around a wavelength of 550 nm also contributes to the emphasized display of outer-layer blood vessels. For this reason, by irradiating the subject with not only light having a wavelength around 415 nm, but also special light having a high intensity around a wavelength of 550 nm, which is another peak in the light absorption rate of hemoglobin, it is possible to increase the luminance in the captured image while also maintaining emphasis of the outer-layer blood vessels.

More specifically, in the special observation mode, by using narrow band light (special light) having peaks at special wavelengths, it is possible to perform narrow band observation that is suited to clearly grasping the paths of blood vessels that are difficult to observe in the normal observation mode (blood vessels in various layers such as the outer layer, middle layer, and deep layer). Performing narrow band observation obtains information that is useful to the early discovery of issues such as cancer.

Figure 4:
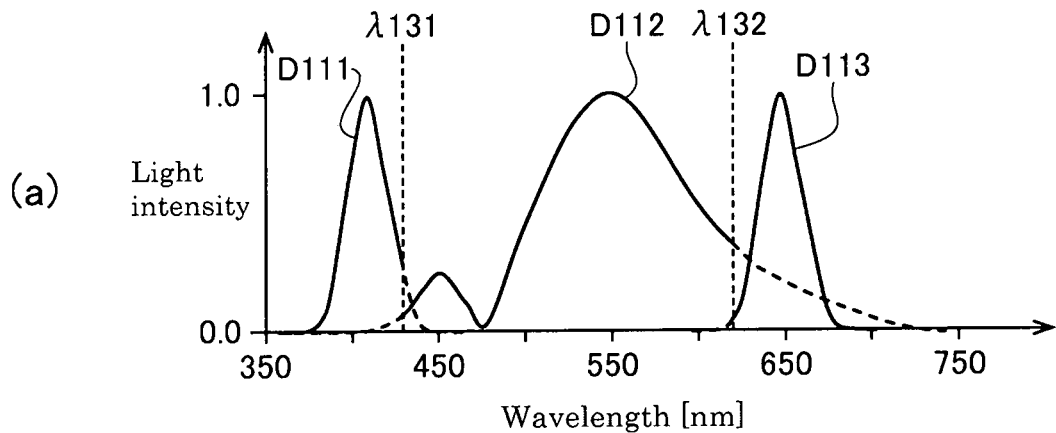
FIG. 4 is a diagram showing a spectral intensity distribution of irradiation light emitted from the endoscope light source device according to the first embodiment of the present disclosure.
Figure 4:
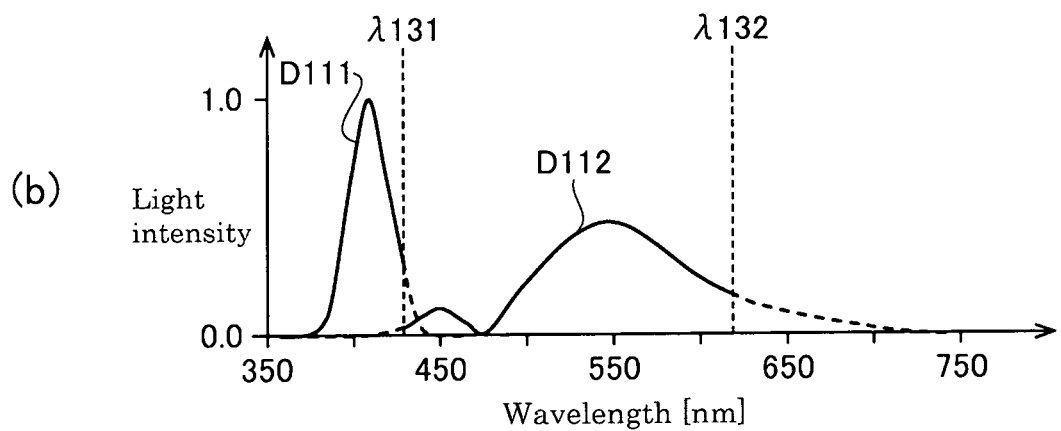

FIG. 4 shows the spectral intensity distributions of the irradiation light L emitted from the light source device 201 in respective observation modes. FIG. 4(a) shows the spectral intensity distribution of the irradiation light L (normal light) in the normal observation mode, and FIG. 4(b) shows the spectral intensity distribution of irradiation light L (special light) in the special observation mode. In FIG. 4, the horizontal axis in the spectral intensity distributions indicates the wavelength (nm), and the vertical axis indicates the intensity of the irradiation light L. Note that the vertical axis is standardized such that the maximum intensity value is 1.

When the electronic endoscope system 1 is in the normal observation mode, all of the light source units 111 to 113 are driven to emit light. The LEDs have sharp spectral intensity distributions that have intensity peaks at specific wavelengths. Note that in this application, "peak wavelength" refers to the wavelength having the highest intensity among the specific wavelengths. For example, if there are two or more intensity peaks, the peak wavelength is the one of them that has the highest intensity. A spectral intensity distribution D111 of light emitted from the first light source unit 111 has a sharp intensity distribution with a peak wavelength at approximately 415 nm. Also, a spectral intensity distribution D113 of light emitted from the third light source unit 113 has a sharp intensity distribution with a peak wavelength at approximately 650 nm.

Also, a spectral intensity distribution D112 of light emitted from the second light source unit 112 has peaks at wavelengths of approximately 450 nm and approximately 550 nm. These two peaks are respectively the peak in the spectral intensity distribution of light emitted from the blue LED 112*a* and the spectral intensity distribution of fluorescent light emitted by the green phosphor 112*b*. The spectral intensity distribution of fluorescent light is largely dependent on the material that is used, and spans a wider wavelength band than the spectral intensity distribution of LED light. The green phosphor 112*b* in the first embodiment has a spectral intensity distribution with a peak wavelength at approximately 550 nm. Note that as shown in FIG. 4(*a*), the peak wavelength of the second light source unit 112 is approximately 550 nm.

Note that in the spectral intensity distribution D112 shown in FIG. 4(*a*), the percentage of the intensity of green fluorescent light intensity is higher than that of the blue LED light, but the present disclosure is not limited to this. The percentages of the blue LED light and the green fluorescent light emitted from the second light source unit 112 can be freely changed by changing the type of green phosphor 112*b* and the amount thereof. Also, although the second light source unit 112 has the green phosphor lib that emits green fluorescent light, the present embodiment is not limited to this. For example, instead of a green phosphor, the second light source unit 112 may have a yellow phosphor that emits yellow fluorescent light having a peak wavelength around 600 nm.

Also, although the spectral intensity distributions D111 to D113 shown in FIG. 4(*a*) are standardized with a maximum intensity value of 1, the present disclosure is not limited to this. The ratio of the intensity of light emitted from the light sources units 111 to 113 can be set according to the observation subject, the imaging mode, or the operator's preference.

Also, in FIG. 4(*a*), cutoff wavelengths λ131 and λ132 of the dichroic mirrors 131 and 132 are shown by dashed lines. The dichroic mirror 131 has the cutoff wavelength λ131 of approximately 430 nm, allows the passage of light with wavelengths shorter than the cutoff wavelength λ131, and reflects light with wavelengths longer than or equal to the cutoff wavelength λ131. For this reason, in the spectral intensity distribution D111 shown in FIG. 4(*a*), light in the wavelength band indicated by a solid line passes through the dichroic mirror 131, and light in the wavelength band indicated by a dashed line is reflected by the dichroic mirror 131. Also, in the spectral intensity distribution D112 shown in FIG. 4(*a*), light with wavelengths that are longer than or equal to the cutoff wavelength λ131 and indicated by a solid line is reflected by the dichroic mirror 131, and light with wavelengths that are than the cutoff wavelength λ131 and indicated by a dashed line passes through the dichroic mirror 131.

Also, the dichroic mirror 132 has the cutoff wavelength λ132 of approximately 620 nm, allows the passage of light with wavelengths shorter than the cutoff wavelength λ132, and reflects light with wavelengths longer than or equal to the cutoff wavelength λ132. For this reason, in the spectral intensity distributions D111 and D112 shown in FIG. 4(*a*), light with wavelengths that are shorter than the cutoff wavelength λ131 and indicated by the solid lines passes through the dichroic mirror 132. Also, in the spectral intensity distribution D112 shown in FIG. 4(*a*), light with wavelengths that are longer than or equal to the cutoff wavelength λ132 and indicated by a dashed line is reflected by the dichroic mirror 132. Also, in the spectral intensity distribution D113 shown in FIG. 4, light with wavelengths that are longer than or equal to the cutoff wavelength λ132 and indicated by a solid line is reflected by the dichroic mirror 132, and light with wavelengths that are shorter than the cutoff wavelength λ132 and indicated by a dashed line passes through the dichroic mirror 132.

In this way, the light paths of light emitted from the light source units 111 to 113 are combined by the dichroic mirror 131 and the dichroic mirror 132, and therefore the light source device 201 emits the irradiation light L (normal light) that has a wide wavelength range spanning from the ultraviolet region (part of the near ultraviolet region) to the red region. The spectral intensity distribution of this irradiation light L (normal light) is the combination of the regions indicated by solid lines in the spectral intensity distributions D111 to D113 shown in FIG. 4(*a*). Irradiating the subject with the irradiation light L (normal light) makes it possible to obtain a normal color captured image.

Also, when the electronic endoscope system 1 is in the special observation mode, the first light source unit 111 and the second light source unit 112 are driven to emit light, and the third light source unit 113 is not driven to emit light. Moreover, the second light source unit 112 is driven to emit light with a smaller drive current and lower intensity than in the normal observation mode. Accordingly, the intensity at the wavelength of approximately 415 nm, which is the peak of the light absorption rate of hemoglobin, is relatively higher than the intensity in the other wavelength bands (i.e., the light is narrow band light), and it is possible to obtain a captured image in which outer-layer blood vessels are emphasized. Also, the light emitted from the second light source unit 112 includes light with a wavelength of approximately 550 nm, which is another peak of the light absorption rate of hemoglobin. For this reason, by driving the second light source unit 112 to emit light in addition to the first light source unit 111, it is possible to raise the luminance in the captured image while also maintaining the emphasis of outer-layer blood vessels.

In this way, according to the first embodiment, the light source device 201 has multiple light sources units 111 to 113 that emit light in mutually different wavelength bands. Also, the light source units 111 to 113 are separately driven to emit light according to the imaging mode. For this reason, by selecting the light source units that are to be driven to emit light and also changing the drive currents of the light source units, it is possible to switch the spectral intensity characteristics of the irradiation light L to characteristics that are in accordance with the observation mode.

Also, the light paths of the light emitted from the light source units 111 to 113 are combined by the dichroic mirrors 131 and 132. Here, the wavelength bands of the light emitted from the light source units 111 to 113 are different from each other, and therefore it is possible to minimize the loss of light when the light paths are combined by the dichroic mirrors 131 and 132.

For example, in the special observation mode, in the case of using an optical filter that allows the passage of substantially only light in a specific wavelength band as in conventional technology, it is necessary for light in wavelength bands other than the specific one to be wastefully emitted, and the light use efficiency of the light source device is low. In contrast, in the first embodiment of the present disclosure, as shown in FIG. 4, due to the combination of the light paths by the dichroic mirrors 131 and 132, the amount of light that is not used as the irradiation light L (the light in the regions indicated by dashed lines in FIG. 4) is smaller than the amount of light that is used as the irradiation light L (the light in the regions indicated by solid lines in FIG. 4). For this reason, with the light source device 201 of the present embodiment, it is not necessary to wastefully emit light in wavelength bands that will not be used in irradiation of the subject, and a higher light use efficiency than in conventional technology can be achieved.

Also, in the case of observing a site that has a relatively large space (e.g., the stomach), the distance from the distal end portion of the electronic endoscope 100 to the subject (e.g., the stomach wall) is typically long, and the subject is irradiated with a lower intensity of irradiation light. In order to obtain a bright captured image, the subject needs to be irradiated with high-intensity irradiation light. The light source device 201 of the present embodiment does not use an optical filter in the special observation mode, and has a high light use efficiency, thus making it possible to increase the intensity of the irradiation light with which the subject is irradiated. For this reason, it is possible to obtain a bright captured image even when observing a site such as the stomach.

Also, although the first light source unit 111 is a purple LED that emits light having a peak wavelength at approximately 415 nm in the first embodiment, the present disclosure is not limited to this. The light emitted from the first light source unit 111 need only include light with a wavelength of 415 nm, which is the peak of the light absorption rate of hemoglobin, and the first light source unit 111 may be an LED that emits light with a peak wavelength at 405 nm, for example. Also, the characteristics of the LEDs and the phosphor of the light source device 201 can be appropriately changed according to the subject of observation.

Note that the following are examples of the phosphor in the present embodiment. Two main types are oxide-based phosphors are nitride-based phosphors.

Oxide-Based Phosphors
  Yellow phosphors
    Yellow phosphor having $Y_3Al_5O_{12}$ (yttrium aluminum oxide) as a host crystal
  Green phosphors
    Green phosphor having $Ca_3Sc_2Si_3O_{12}$ (calcium scandium silicon oxide) as a host crystal and activated with Ce
    Green phosphor having $CaSc_2O_4$ (calcium scandium oxide) as a host crystal and activated with Ce
Nitride-Based Phosphors
  Red phosphors
    Red phosphor in which silicon oxynitride ($Si_2N_2O$) is dissolved into calcium aluminum silicon nitride ($CaAlSiN_3$) activated with Eu as a host crystal
  Other phosphors
    e.g., a sialon phosphor having a ceramic crystal as a matrix and having a micro-addition of a metal ion that performs light emission such as a rear earth element, an α-sialon phosphor that is a solid solution of an α-type silicon nitride ($Si_3N_4$) crystal, and a calcium aluminum silicon nitride phosphor Second Embodiment Next, an endoscope light source device according to a second embodiment of the present disclosure will be described. The light source device according to the second embodiment is also used in the electronic endoscope system 1, similarly to the light source device 201 according to the first embodiment.

Figure 5:
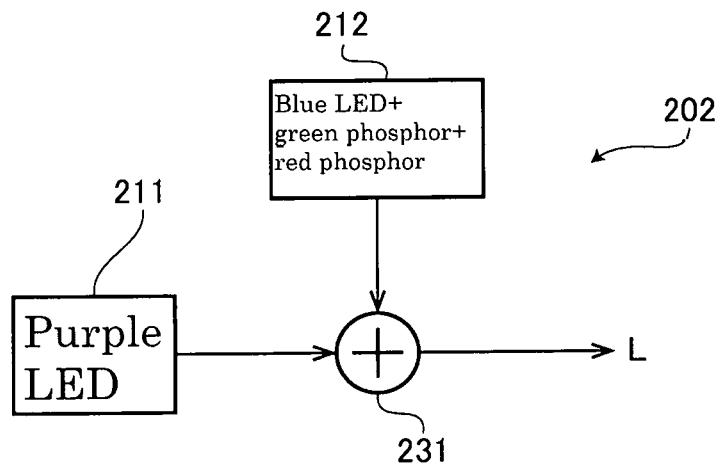
FIG. 5 is a block diagram of an endoscope light source device according to a second embodiment of the present disclosure.

FIG. 5 is a block diagram conceptually showing only light source units and a dichroic mirror in a light source device 202 according to the second embodiment. The light source device 202 includes a first light source unit 211, a second light source unit 212, and a dichroic mirror 231. The emission of light from the light source units 211 and 212 is separately controlled by a first light source drive circuit and a second light source drive circuit, respectively, which are not shown in the figure.

The first light source unit 211 is a purple LED that emits light in the purple wavelength band (e.g., wavelengths of 395 to 435 nm). The second light source unit 212 has a blue LED that emits light in the blue wavelength band (e.g., wavelengths of 430 to 490 nm), a green phosphor, and a red phosphor. The green phosphor is excited by blue LED light emitted from the blue LED and emits fluorescent light in the green wavelength band (e.g., wavelengths of 460 to 600 nm). The red phosphor is excited by blue LED light emitted from the blue LED and emits fluorescent light in the red wavelength band (e.g., wavelengths of 550 to 750 nm). Note that the green phosphor and the red phosphor may be arranged side-by-side along the emission direction of the blue LED light, or may be arranged side-by-side in a direction perpendicular to the emission direction. Also, the materials of the green phosphor and the red phosphor may be combined to create a single phosphor.

A collimator lens (not shown) is arranged in front of, with respect to the emission direction, each of the light source units 211 and 212. The purple LED light emitted from the first light source unit 211 is converted into parallel light by the corresponding collimator lens, and is incident on the dichroic mirror 231. Also, the light emitted from the second light source unit 212, that is to say the blue LED light and the green and red fluorescent light, is converted into parallel light by the corresponding collimator lens, and is incident on the dichroic mirror 231. The dichroic mirror 231 combines the light path of the light emitted from the first light source unit 211 and the light path of the light emitted from the second light source unit 212. The light path of the light combined by the dichroic mirror 231 is emitted from the light source device 202 as the irradiation light L.

Figure 6:
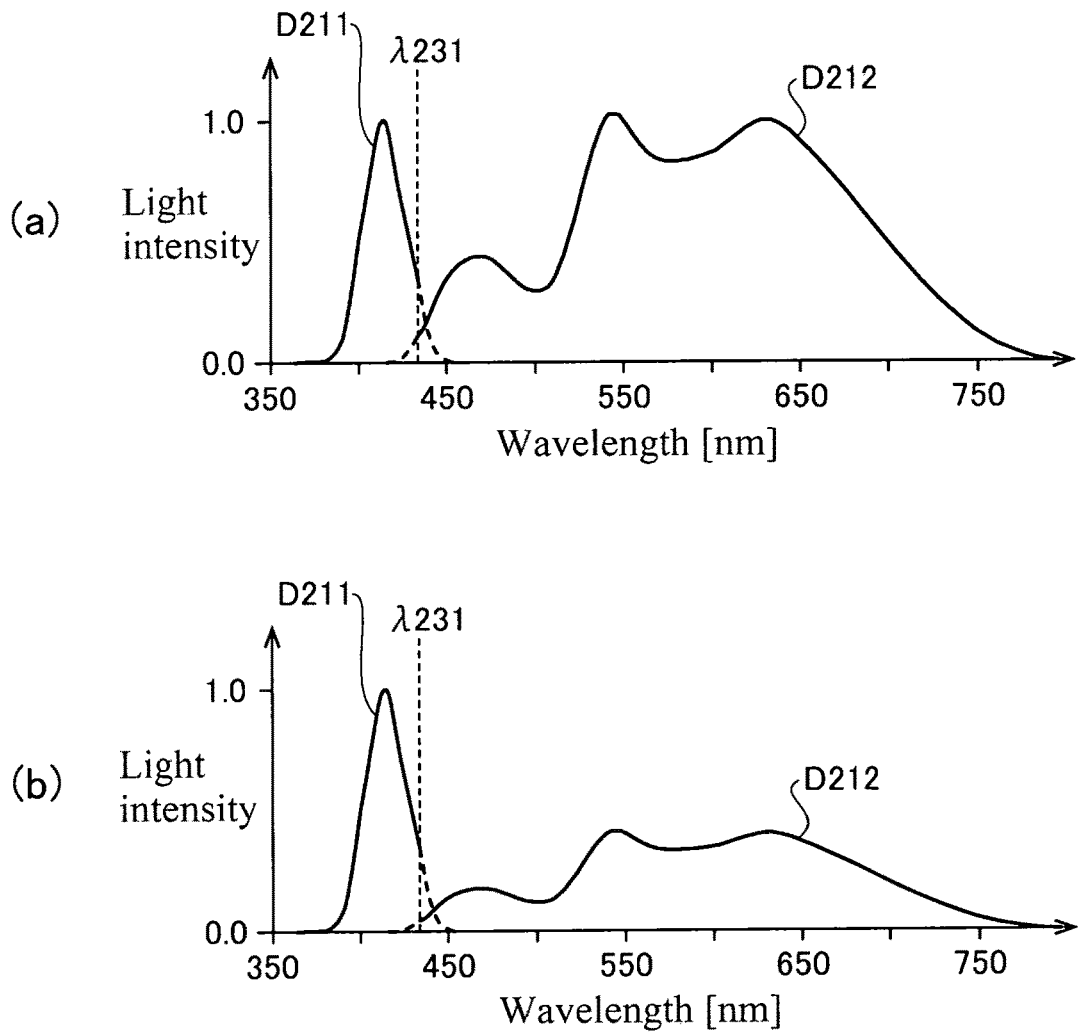
FIG. 6 is a diagram showing a spectral intensity distribution of irradiation light emitted from the endoscope light source device according to the second embodiment of the present disclosure.

FIG. 6 shows the spectral intensity distributions of the irradiation light L emitted from the light source device 202 in respective observation modes, similarly to FIG. 4.

When the electronic endoscope system 1 is in the normal observation mode, both the light source unit 211 and the light source unit 212 are driven to emit light. A spectral intensity distribution D211 of light emitted from the first light source unit 211 has a sharp intensity distribution with a peak wavelength at approximately 415 nm. A spectral intensity distribution D212 of light emitted from the second light source unit 212 has peaks at wavelengths of approximately 470 nm, approximately 550 nm, and approximately 630 nm. These three wavelengths are respectively the peak wavelengths of blue LED light, green fluorescent light, and red fluorescent light.

Also, in FIG. 6(a), a cutoff wavelength λ231 of the dichroic mirror 231 is shown by a dashed line. The dichroic mirror 231 has the cutoff wavelength λ231 of approximately 430 nm, allows the passage of light with wavelengths shorter than the cutoff wavelength λ231, and reflects light with wavelengths longer than or equal to the cutoff wavelength λ231. For this reason, in the spectral intensity distribution D211 shown in FIG. 4(a), light in the wavelength band indicated by a solid line passes through the dichroic mirror 231, and light in the wavelength band indicated by a dashed line is reflected by the dichroic mirror 231. Also, in the spectral intensity distribution D212 shown in FIG. 4(a), light in the wavelength band indicated by a solid line passes through the dichroic mirror 231, and light in the wavelength band indicated by a dashed line is reflected by the dichroic mirror 231.

In this way, the light paths of light emitted from the light source units 211 and 212 are combined by the dichroic mirror 231, and therefore the light source device 202 emits the irradiation light L (normal light) that has a wide wavelength range spanning from the ultraviolet region (part of the near ultraviolet region) to the red region. The spectral intensity distribution of this irradiation light L (normal light) is the combination of the regions indicated by solid lines in the spectral intensity distributions D211 and D212 shown in FIG. 6(a). Irradiating the subject with this irradiation light L (normal light) makes it possible to obtain a normal color captured image.

Also, when the electronic endoscope system 1 is in the special observation mode, both the first light source unit 211 and the second light source unit 212 are driven to emit light. Moreover, the second light source unit 212 is driven to emit light with a smaller drive current and lower intensity than in the normal observation mode. Accordingly, in the irradiation light L (special light), the intensity at the wavelength of approximately 415 nm, which is the peak of the light absorption rate of hemoglobin, is relatively higher than the intensity in the other wavelength bands (i.e., the light is narrow band light), and it is possible to obtain a captured image in which outer-layer blood vessels are emphasized. Also, the light emitted from the second light source unit 212 includes light with a wavelength of approximately 550 nm, which is another peak of the light absorption rate of hemoglobin. For this reason, by driving the light source unit 212 to emit light in addition to the light source unit 211, it is possible to raise the luminance in the captured image while also maintaining the emphasis of outer-layer blood vessels.

In this way, according to the second embodiment, the light source device 202 has multiple light sources units 211 and 212 that emit light in mutually different wavelength bands. Also, the light source units 211 and 212 are separately driven to emit light. For this reason, it is possible to obtain irradiation light L that has a desired spectral intensity distribution by selecting the light source units that are to be driven to emit light according to the observation mode, and changing the drive currents of the light source units.

Also, the light source device 202 of the second embodiment has only two light source units, thus making it possible to simplify the configuration of the light source device 202. Moreover, the second light source unit 212 has two phosphors, namely green and red phosphors. For this reason, when the electronic endoscope system 1 is in the normal observation mode, the spectral intensity distribution of the irradiation light L (normal light) more closely approaches a flat distribution in the visible region than in the case where the second light source unit 212 has one phosphor. Accordingly, the subject can be irradiated with irradiation light L (normal light) that is close to natural white light.

Third Embodiment

Next, an endoscope light source device according to a third embodiment of the present disclosure will be described. The light source device according to the third embodiment is also used in the electronic endoscope system 1, similarly to the light source device 201 according to the first embodiment.

Figure 7:
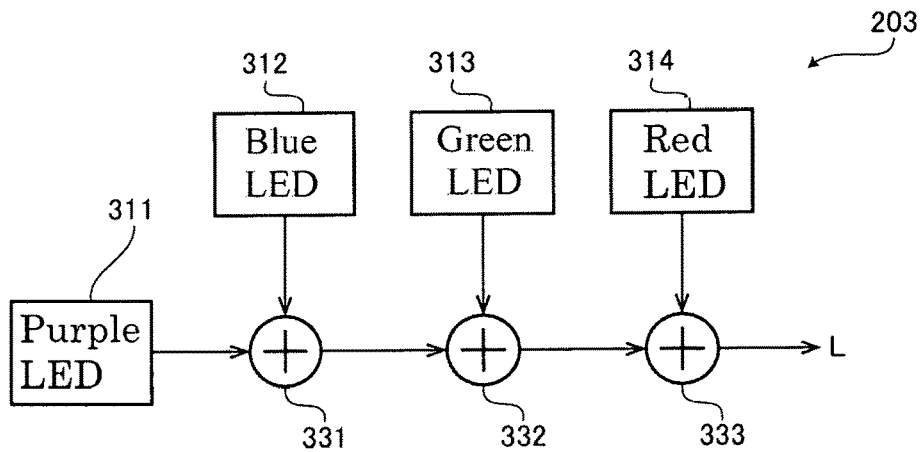
FIG. 7 is a block diagram of an endoscope light source device according to a third embodiment of the present disclosure.

FIG. 7 is a block diagram conceptually showing only light source units and dichroic mirrors in a light source device 203 according to the third embodiment. The light source device 203 includes first to fourth light source units 311 to 314 and first to third dichroic mirrors 331 to 333. The emission of light from the light source units 311 to 314 is separately controlled by first to fourth light source drive circuits, respectively, which are not shown in the figure.

The first light source unit 311 is a purple LED that emits light in the purple wavelength band (e.g., wavelengths of 395 to 435 nm). The second light source unit 312 is a blue LED that emits light in the blue wavelength band (e.g., wavelengths of 430 to 470 nm). The third light source unit 313 is a green LED that emits light in the green wavelength band (e.g., wavelengths of 530 to 570 nm). The fourth light source unit 314 is a red LED that emits light in the red wavelength band (e.g., wavelengths of 630 to 670 nm).

A collimator lens (not shown) is arranged in front of, with respect to the emission direction, each of the light source units 311 to 314. The purple LED light emitted from the first light source unit 311 is converted into parallel light by the corresponding collimator lens, and is incident on the dichroic mirror 331. Also, the light emitted from the second light source unit 312, that is to say the blue LED light, is converted into parallel light by the corresponding collimator lens, and is incident on the dichroic mirror 331. The dichroic mirror 331 combines the light path of the light emitted from the first light source unit 311 and the light path of the light emitted from the second light source unit 312. The light on the light paths combined by the dichroic mirror 331 is incident on the dichroic mirror 332.

Also, the green LED light emitted from the third light source unit 313 is converted into parallel light by the corresponding collimator lens, and is incident on the dichroic mirror 332. The dichroic mirror 332 combines the light path of light from the dichroic mirror 331 and the light path of light emitted from the third light source unit 313. The light on the light paths combined by the dichroic mirror 332 is incident on the dichroic mirror 333.

Also, the red LED light emitted from the fourth light source unit 314 is converted into parallel light by the corresponding collimator lens, and is incident on the dichroic mirror 333. The dichroic mirror 333 combines the light path of light from the dichroic mirror 332 and the light path of light emitted from the fourth light source unit 314. The light path of the light combined by the dichroic mirror 333 is emitted from the light source device 203 as the irradiation light L.

Figure 8:
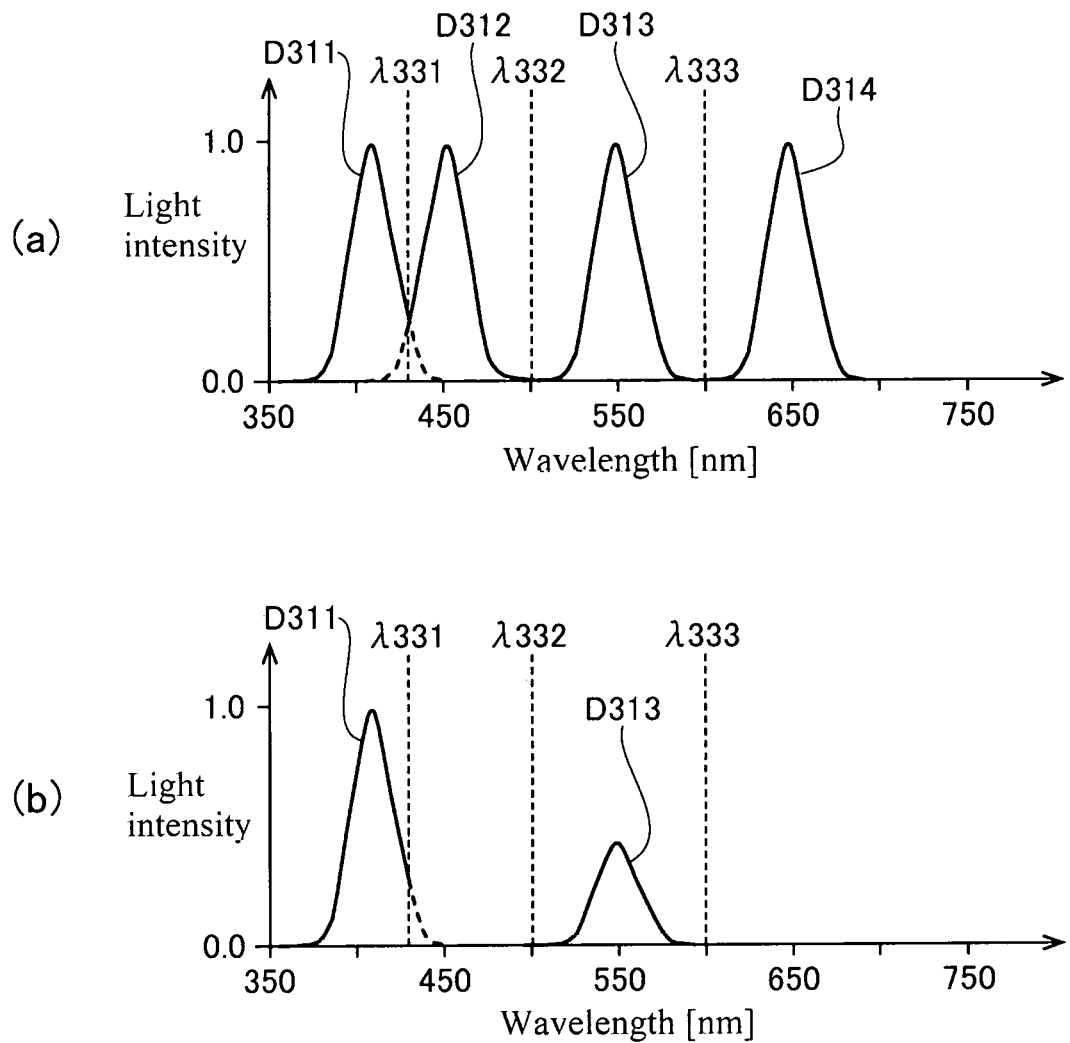
FIG. 8 is a diagram showing a spectral intensity distribution of irradiation light emitted from the endoscope light source device according to the third embodiment of the present disclosure.

FIG. 8 shows the spectral intensity distributions of the irradiation light L emitted from the light source device 203 in respective observation modes, similarly to FIG. 4.

When the electronic endoscope system 1 is in the normal observation mode, the first to fourth light source units 311 to 314 are all driven to emit light. A spectral intensity distribution D311 of the first light source unit 311 has a sharp intensity distribution with a peak wavelength at approximately 415 nm. A spectral intensity distribution D312 of the second light source unit 312 has a sharp intensity distribution with a peak wavelength at approximately 450 nm. A spectral intensity distribution D313 of the third light source unit 313 has a sharp intensity distribution with a peak wavelength at approximately 550 nm. A spectral intensity distribution D314 of the fourth light source unit 314 has a sharp intensity distribution with a peak wavelength at approximately 650 nm. Also, in FIG. 8(a), cutoff wavelengths $\lambda 331$ to $\lambda 333$ of the dichroic mirrors 331 to 333 are shown by dashed lines. The cutoff wavelengths $\lambda 331$ to $\lambda 333$ are respectively 430 nm, 500 nm, and 600 nm. The dichroic mirrors 331 to 333 each allow the passage of light with wavelengths shorter than the cutoff wavelength, and reflect light with wavelengths longer than or equal to the cutoff wavelength. The light paths of light emitted from the light source units 311 to 314 are combined by the dichroic mirrors 331 to 333.

In this way, the light paths of light emitted from the light source units 311 to 314 are combined by the dichroic mirrors 331 to 333, and therefore the light source device 203 emits the irradiation light L (normal light) that has a wide wavelength range spanning from the ultraviolet region (part of the near ultraviolet region) to the red region. The spectral intensity distribution of this irradiation light L (normal light) is the combination of the regions indicated by solid lines in the spectral intensity distributions D311 to D314 shown in FIG. 8(a). Irradiating the subject with this irradiation light L (normal light) makes it possible to obtain a normal color captured image.

Also, when the electronic endoscope system 1 is in the special observation mode, the first light source unit 311 and the third light source unit 313 are driven to emit light, and the second light source unit 312 and the fourth light source unit 314 are not driven to emit light. Moreover, the third light source unit 313 is driven to emit light with a smaller drive current and lower intensity than in the normal observation mode. Accordingly, in the irradiation light L (special light), the intensity at the wavelength of approximately 415 nm, which is the peak of the light absorption rate of hemoglobin, is relatively higher than the intensity in the other wavelength bands (i.e., the light is narrow band light), and it is possible to obtain a captured image in which outer-layer blood vessels are emphasized. Also, the light emitted from the light source unit 313 includes light with a wavelength of approximately 550 nm, which is another peak of the light absorption rate of hemoglobin. For this reason, by driving the light source unit 312 to emit light in addition to the light source unit 311, it is possible to raise the luminance in the captured image while also maintaining the emphasis of outer-layer blood vessels.

In this way, according to the third embodiment, multiple light source units 311 to 314 are provided and emit light in mutually different wavelength bands. Also, the light source units 311 to 314 are separately driven to emit light. For this reason, it is possible to obtain irradiation light L that has a desired spectral intensity distribution by selecting the light source units that are to be driven to emit light according to the observation mode, and changing the drive currents of the light source units.

Also, the light source device 203 of the third embodiment has the four light source units 311 to 314 that have different wavelength bands and can be separately controlled to emit light. For this reason, it is possible to finely control the spectral intensity distribution of the irradiation light L by selecting the light source units that are to be driven to emit light from among the four light source units 311 to 314, and separately controlling the drive currents when driving the light source units to emit light.

Note that in the third embodiment, when the electronic endoscope system 1 is in the special observation mode, the second light source unit 312 may be driven to emit light with a smaller drive current and lower intensity than when in the normal observation mode. Because hemoglobin has a peak in the light absorption rate at approximately 415 nm, it has a relatively high light absorption also in the nearby blue wavelength band. For this reason, when in the special observation mode, if the second light source unit 312, which emits light in the blue wavelength band, is driven to emit light, it is possible to increase the luminance in the captured image while also improving the effect of emphasizing outer-layer blood vessels in the captured image.

Fourth Embodiment

Figure 9:
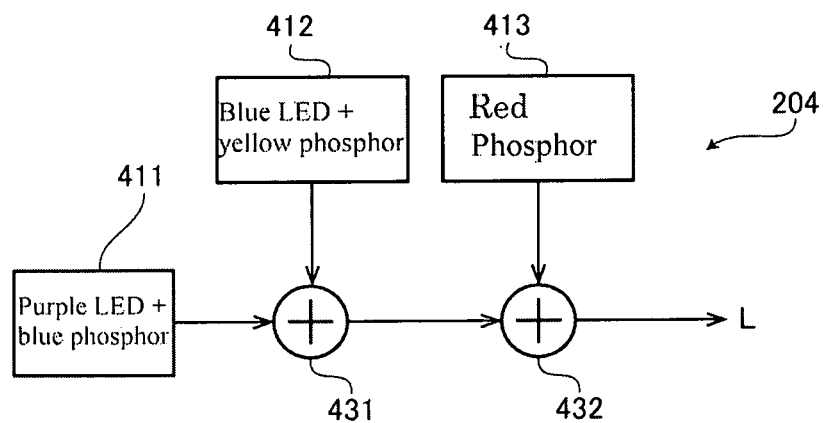
FIG. 9 is a block diagram of an endoscope light source device according to a fourth embodiment of the present disclosure.

In the first to third embodiments, the light source units are divided into a light source unit that emits light in the purple wavelength band (a purple LED) and a light source unit that emits light in other wavelength bands, but the present disclosure is not limited to this. For example, the purple LED may include a phosphor. FIG. 9 is a block diagram conceptually showing only light source units and dichroic mirrors in a light source device 204 according to the fourth embodiment of the present disclosure. The light source device 204 according to the fourth embodiment is also used in the electronic endoscope system 1 for example, similarly to the light source device 201 according to the first embodiment.

As shown in FIG. 9, the light source device 204 includes first to third light source units 411 to 413 and first and second dichroic mirrors 431 and 432. The emission of light from the light source units 411 to 413 is separately controlled by first to third light source drive circuits, respectively, which are not shown in the figure.

The first light source unit 411 has a purple LED that emits light in the purple wavelength band (e.g., wavelengths of 395 to 435 nm), and a blue phosphor that is excited by purple LED light so as to emit blue (e.g., wavelengths of 430 to 490 nm) fluorescent light. The second light source unit 412 has a blue LED that emits light in the blue wavelength band (e.g., wavelengths of 430 to 470 nm), and a yellow phosphor that is excited by blue LED light emitted from the blue LED so as to emit fluorescent light in the yellow wavelength band (e.g., wavelengths of 500 to 720 nm). The third light source unit 413 has a red LED that emits light in the red wavelength band (e.g., wavelengths of 620 to 680 nm).

A collimator lens (not shown) is arranged in front of, with respect to the emission direction, each of the light source units 411 to 413. The purple LED light and the blue fluorescent light emitted from the first light source unit 411 is converted into parallel light by the corresponding collimator lens, and is incident on the dichroic mirror 431. Also, the blue LED light and the yellow fluorescent light emitted from the second light source unit 412 is converted into parallel light by the corresponding collimator lens, and is incident on the dichroic mirror 431. The dichroic mirror 431 combines the light path of the light emitted from the first light source unit 411 and the light path of the light emitted from the second light source unit 412. The light on the light paths combined by the dichroic mirror 431 is incident on the dichroic mirror 432.

Also, the red LED light emitted from the third light source unit 413 is converted into parallel light by the corresponding collimator lens, and is incident on the dichroic mirror 432. The dichroic mirror 432 combines the light path of light from the dichroic mirror 431 and the light path of light emitted from the third light source unit 413. The light path of the light combined by the dichroic mirror 432 is emitted from the light source device 204 as the irradiation light L.

Figure 10:
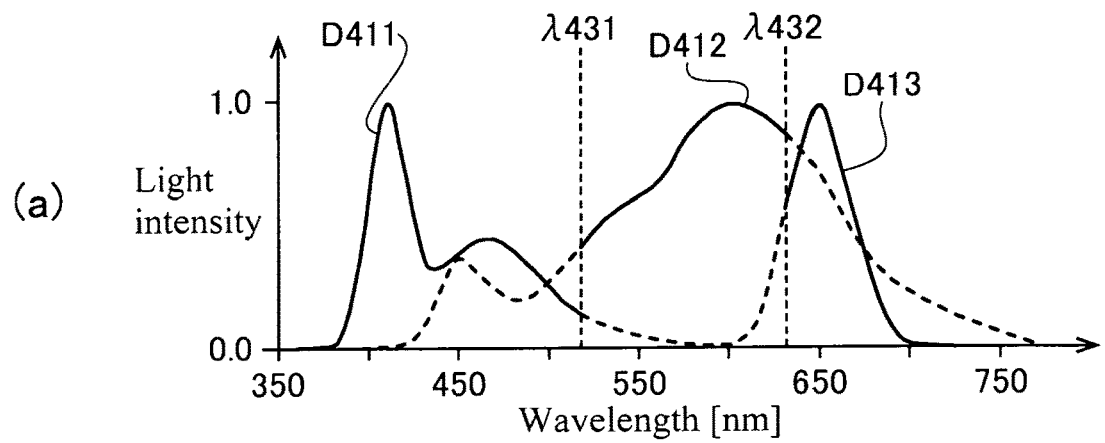
FIG. 10 is a diagram showing a spectral intensity distribution of irradiation light emitted from the endoscope light source device according to the fourth embodiment of the present disclosure.

FIG. 10 shows the spectral intensity distributions of the irradiation light L emitted from the light source device 204 in respective observation modes, similarly to FIG. 4.

When the electronic endoscope system 1 is in the normal observation mode, the first to third light source units 411 to 413 are all driven to emit light. A spectral intensity distribution D411 of the first light source unit 411 has peak wavelengths at approximately 415 nm and 470 nm. These two wavelengths are respectively the peak wavelengths in the spectral intensity distributions of purple LED light and blue fluorescent light. Here, in the spectral intensity distribution D411, the height of the peak wavelength at approximately 415 nm is set higher than the height of the peak wavelength at approximately 470 nm. A spectral intensity distribution D421 of the second light source unit 412 has peak wavelengths at approximately 450 nm and 600 nm. These two wavelengths are respectively the peak wavelengths of blue LED light and yellow fluorescent light. A spectral intensity distribution D413 of the third light source unit 413 has a sharp intensity distribution with a peak wavelength at approximately 650 nm.

Also, in FIG. 10(a), cutoff wavelengths λ431 and λ432 of the dichroic mirrors 431 and 432 are shown by dashed lines. The cutoff wavelengths λ431 and λ432 are respectively 520 nm and 630 nm. The dichroic mirrors 431 and 432 each allow the passage of light with wavelengths shorter than the cutoff wavelength, and reflect light with wavelengths longer than or equal to the cutoff wavelength. The light paths of light emitted from the light source units 411 to 413 are combined by the dichroic mirrors 431 and 432. Note that in the light emitted from the second light source unit 412, the blue LED light having a peak wavelength at approximately 450 nm is shorter than the cutoff wavelength λ431, and therefore is not included in the light whose light path is combined with another light path by the dichroic mirror 431.

In this way, the light paths of light emitted from the light source units 411 to 413 are combined by the dichroic mirrors 431 and 432, and therefore the light source device 204 emits the irradiation light L (normal light) that has a wide wavelength range spanning from the ultraviolet region (part of the near ultraviolet region) to the red region. The spectral intensity distribution of this irradiation light L (normal light) is the combination of the regions indicated by solid lines in the spectral intensity distributions D411 to D413 shown in FIG. 10(a). Irradiating the subject with this irradiation light L (normal light) makes it possible to obtain a normal color captured image.

Also, when the electronic endoscope system 1 is in the special observation mode, the first light source unit 411 and the second light source unit 412 are driven to emit light, and the third light source unit 413 is not driven to emit light. Moreover, the second light source unit 412 is driven to emit light with a smaller drive current and lower intensity than in the normal observation mode. Accordingly, in the irradiation light L (special light), the intensity at the wavelength of approximately 415 nm, which is the peak of the light absorption rate of hemoglobin, is relatively higher than the intensity in the other wavelength bands (i.e., the light is narrow band light), and it is possible to obtain a captured image in which outer-layer blood vessels are emphasized. Also, the light emitted from the second light source unit 412 includes light with a wavelength of approximately 550 nm, which is another peak of the light absorption rate of hemoglobin. For this reason, by driving the second light source unit 412 to emit light in addition to the first light source unit 411, it is possible to raise the luminance in the captured image while also maintaining the emphasis of outer-layer blood vessels.

Note that the biological tissue in the body cavity that is subjected to image capturing in the electronic endoscope system 1 normally has an overall red tint due to blood. For this reason, if the biological tissue is irradiated with red light in the special observation mode, the captured image will have a red tint overall, and it will be difficult to obtain an effect of emphasizing outer-layer blood vessels. In the present embodiment, the red LED (third light source unit 413) is not driven to emit light in the special observation mode, thus making it possible to prevent a reduction in the effect of emphasizing outer-layer blood vessels.

Also, in the present embodiment, in the special observation mode, the subject is irradiated with light in the blue wavelength band emitted from the first light source unit 411. The blue wavelength band does not include a wavelength that is a peak in the light absorption rate of hemoglobin, but is more likely to be absorbed by biological tissue than red light. For this reason, even if the biological tissue is irradiated with blue light in the special observation mode, this has little influence on the effect of emphasizing outer-layer blood vessels. Also, irradiating the subject with blue light makes it possible to raise the luminance in the captured image.

Also, in the present embodiment, in the light emitted from the second light source unit 412, the subject is irradiated with only the yellow fluorescent light, and is not irradiated with the blue LED light. On the other hand, the subject is irradiated with light in the blue wavelength band emitted from the first light source unit 411. For this reason, it is possible to separately change the intensity of light in the blue wavelength band, which has little influence on the effect of emphasizing outer-layer blood vessels, and the intensity of light in the yellow wavelength band, which has a relatively large influence on the same effect. Accordingly, in the special observation mode, it is easy to adjust the balance between the effect of emphasizing outer-layer blood vessels and the brightness of the captured image.

Also, although the second light source unit 412 has a yellow phosphor in the fourth embodiment, the present disclosure is not limited to this. For example, instead of a yellow phosphor, the second light source unit 412 may have a green phosphor that emits green fluorescent light having a peak wavelength around 550 nm.

Fifth Embodiment

Next, an endoscope light source device according to a fifth embodiment of the present disclosure will be described. The light source device according to the fifth embodiment is also used in the electronic endoscope system 1, similarly to the light source device 201 according to the first embodiment.

Figure 11:
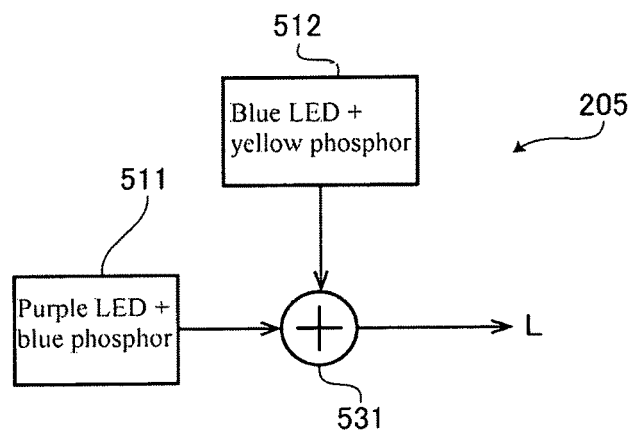
FIG. 11 is a block diagram of an endoscope light source device according to a fifth embodiment of the present disclosure.

FIG. 11 is a block diagram conceptually showing only light source units and a dichroic mirror in a light source device 205 according to the fifth embodiment. The light source device 205 includes a first light source unit 511, a second light source unit 512, and a dichroic mirror 531. The emission of light from the light source units 511 and 512 is separately controlled by a first light source drive circuit and a second light source drive circuit, respectively, which are not shown in the figure. As shown in FIG. 11, the light source device 205 according to the fifth embodiment has a configuration in which the red LED (third light source unit 413) and the dichroic mirror 432 are omitted from the configuration of the light source device 204 according to the fourth embodiment. Also, the characteristics of the first light source unit 511, the second light source unit 512, and the dichroic mirror 531 are the same as the characteristics of the first light source unit 411, the second light source unit 412, and the dichroic mirror 431 of the fourth embodiment.

Figure 12:
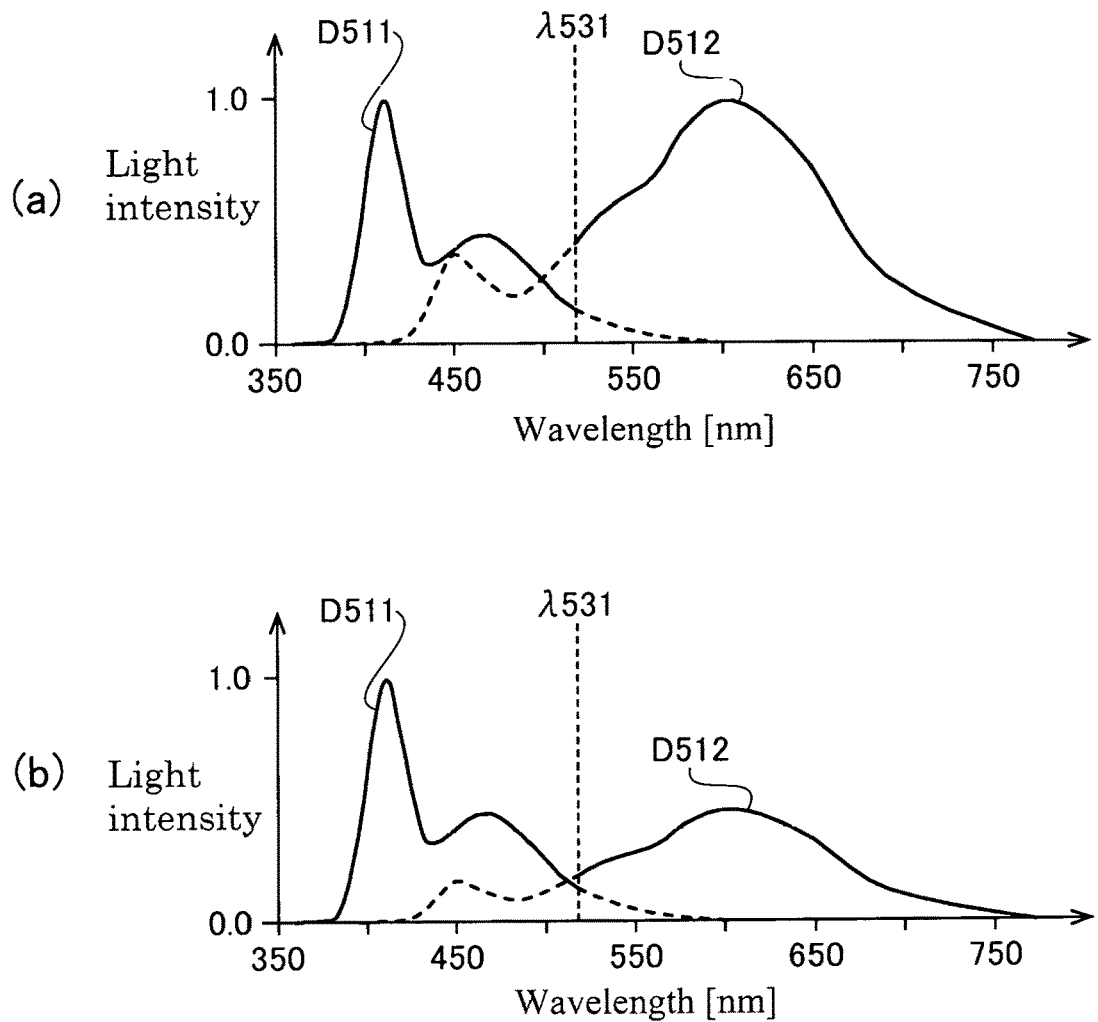
FIG. 12 is a diagram showing a spectral intensity distribution of irradiation light emitted from the endoscope light source device according to the fifth embodiment of the present disclosure.

FIG. 12 shows the spectral intensity distributions of the irradiation light L emitted from the light source device 205 in respective observation modes, similarly to FIG. 4.

As shown in FIG. 12, the spectral intensity distributions of irradiation light L in the fifth embodiment are the same as those of the irradiation light L in the fourth embodiment, with the exception of omitting red LED light. It should be noted that because the light source device 205 of the fifth embodiment does not have the dichroic mirror 432, the irradiated irradiation light L also includes light in the wavelength band of wavelengths greater than or equal to 630 nm in the light emitted from the second light source unit 512.

Compared to the light source device 204 of the fourth embodiment, the light source device 205 of the fifth embodiment can be given a simpler configuration to the extent of omitting the red LED (light source unit 413) and the dichroic mirror 432. Also, in the light source device 205 of the fifth embodiment, light in the red wavelength band of wavelengths longer than 630 nm in the light emitted from the second light source unit 512 is also used as the irradiation light L, thus making it possible to obtain pseudo white irradiation light L (normal light) in the normal observation mode even without a red LED.

Also, although the second light source unit 512 has a yellow phosphor in the fifth embodiment, the present disclosure is not limited to this. For example, similarly to the second light source unit 212 in the second embodiment, the second light source unit 512 may have a green phosphor and a red phosphor instead of a yellow phosphor. In this case, in the normal observation mode, it is possible to obtain normal light that has a wider wavelength band than in the case of using a yellow phosphor.

Sixth Embodiment

Next, an endoscope light source device according to a sixth embodiment of the present disclosure will be described. The light source device according to the sixth embodiment is also used in the electronic endoscope system 1, similarly to the light source device 201 according to the first embodiment.

Figure 13:
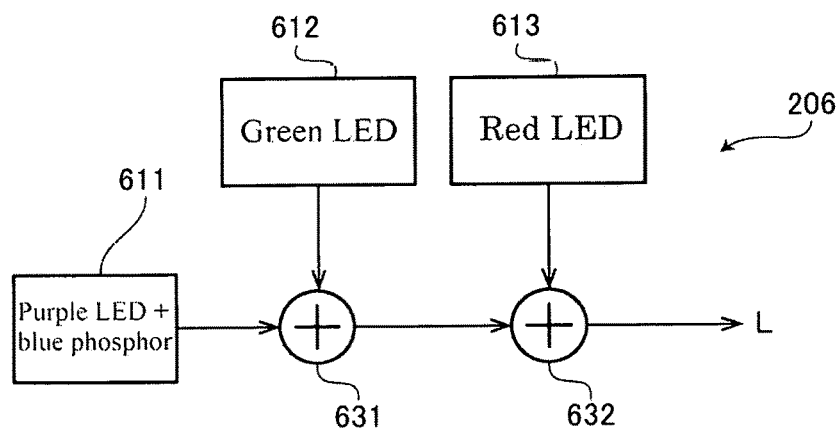
FIG. 13 is a block diagram of an endoscope light source device according to a sixth embodiment of the present disclosure.

FIG. 13 is a block diagram conceptually showing only light source units and dichroic mirrors in a light source device 206 according to the sixth embodiment. The light source device 206 includes first to third light source units 611 to 613 and first and second dichroic mirrors 631 and 632. The emission of light from the light source units 611 to 613 is separately controlled by first to third light source drive circuits, respectively, which are not shown in the figure. As shown in FIG. 13, the light source device 206 according to the sixth embodiment has a configuration in which the blue LED (second light source unit 312) and the dichroic mirror 331 are omitted from the configuration of the light source device 203 according to the third embodiment, and instead the first light source unit 611 is provided with a blue phosphor. Also, the characteristics of the first light source unit 611 are the same as the characteristics of the first light source unit 511 in the fifth embodiment. Moreover, the characteristics of the second light source unit 612, third light source unit 613, the dichroic mirror 631, and the dichroic mirror 632 are respectively the same as the characteristics of the third light source unit 313, the fourth light source unit 314, the dichroic mirror 332, and the dichroic mirror 333 of the third embodiment.

Figure 14:
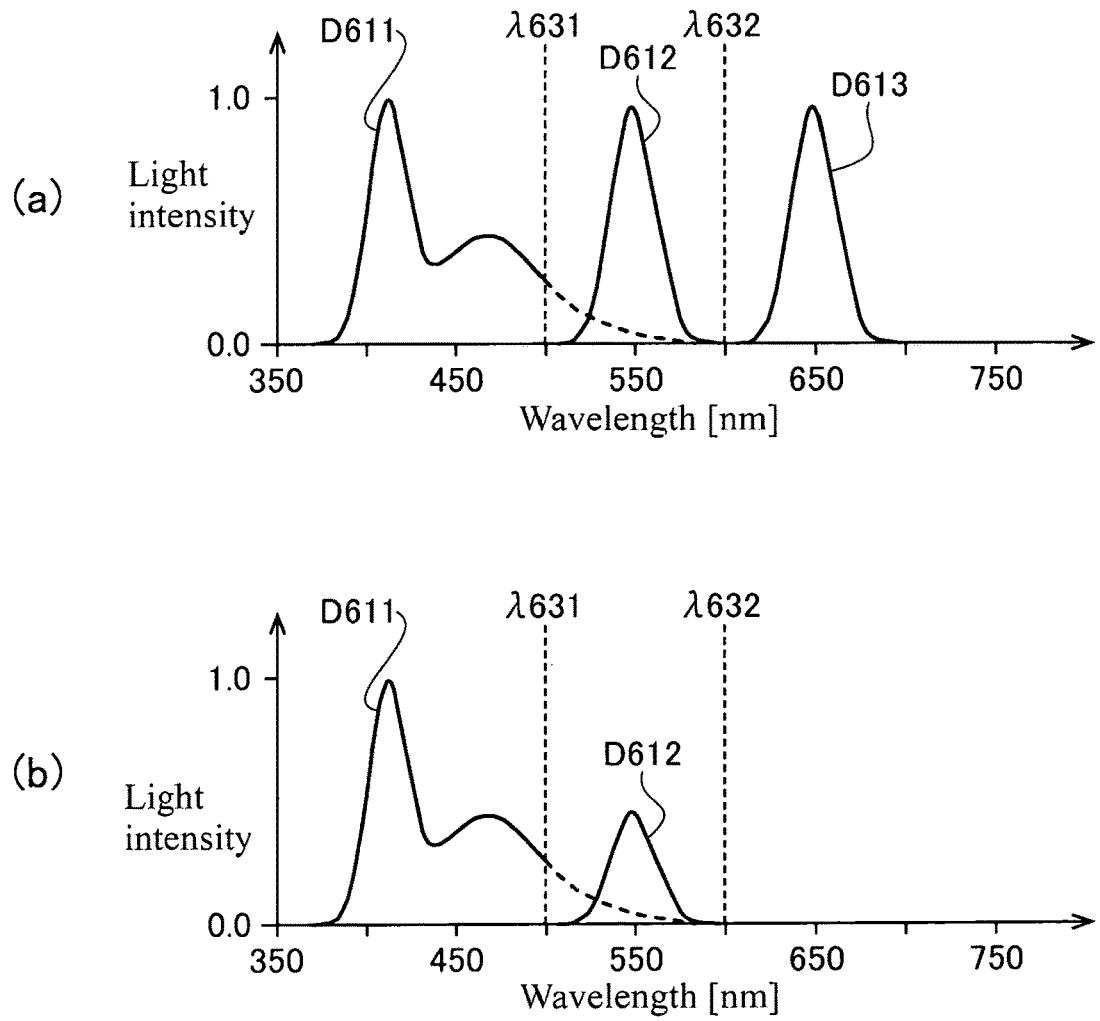
FIG. 14 is a diagram showing a spectral intensity distribution of irradiation light emitted from the endoscope light source device according to the sixth embodiment of the present disclosure.

FIG. 14 shows the spectral intensity distributions of the irradiation light L emitted from the light source device 206 in respective observation modes, similarly to FIG. 4.

As shown in FIG. 14, the spectral intensity distributions of irradiation light L in the sixth embodiment are the same as those of the irradiation light L in the third embodiment, with the exception of omitting purple LED light and blue LED light, and instead adding purple LED light and blue fluorescent light emitted from the first light source unit 611 (D611). It should be noted that because the light source device 206 of the sixth embodiment does not have the dichroic mirror 331, the irradiated irradiation light L also includes light in the wavelength band of wavelengths greater than or equal to the cutoff wavelength λ331 (wavelength of 430 nm) and shorter than a cutoff wavelength λ631 (wavelength of 500 nm) in the light emitted from the first light source unit 611.

Compared to the light source device 203 of the third embodiment, the light source device 206 of the sixth embodiment can be given a simpler configuration to the extent of omitting the blue LED (light source unit 212) and the dichroic mirror 331.

Seventh Embodiment

Next, an endoscope light source device according to a seventh embodiment of the present disclosure will be described. The light source device according to the seventh embodiment is also used in the electronic endoscope system 1, similarly to the light source device 201 according to the first embodiment.

Figure 15:
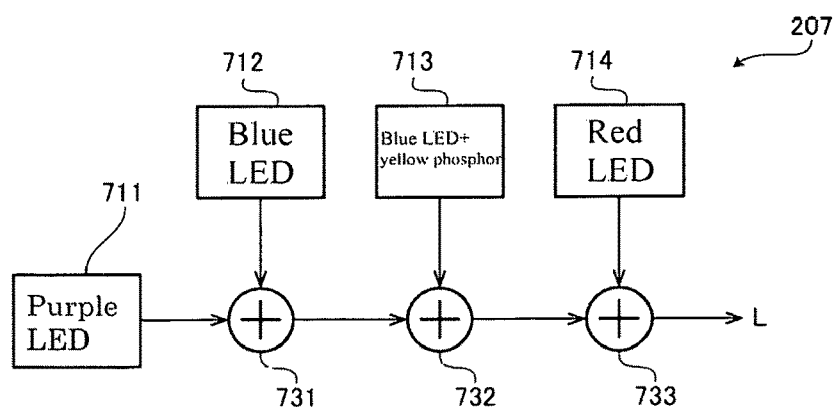
FIG. 15 is a block diagram of an endoscope light source device according to a seventh embodiment of the present disclosure.

FIG. 15 is a block diagram conceptually showing only light source units and dichroic mirrors in a light source device 207 according to the seventh embodiment. The light source device 207 includes first to fourth light source units 711 to 714 and first to third dichroic mirrors 731 to 733. The emission of light from the light source units 711 to 714 is separately controlled by first to fourth light source drive circuits, respectively, which are not shown in the figure. As shown in FIG. 15, the light source device 207 according to the seventh embodiment has a configuration in which the green LED (third light source unit 313) of the light source device 203 according to the third embodiment is replaced with a fluorescent LED that has a blue LED and a yellow phosphor. It should be noted that cutoff wavelengths λ731 to λ733 of the dichroic mirrors 731 to 733 of the seventh embodiment do not need to be the same as λ331 to λ333 of the dichroic mirrors 331 to 333 of the third embodiment. Specifically, the cutoff wavelengths λ731 to λ733 may be appropriately set so as to reduce light loss during the combination of light paths by the dichroic mirrors 731 to 733, or so as to obtain a desired spectral intensity distribution for the irradiation light L.

Figure 16:
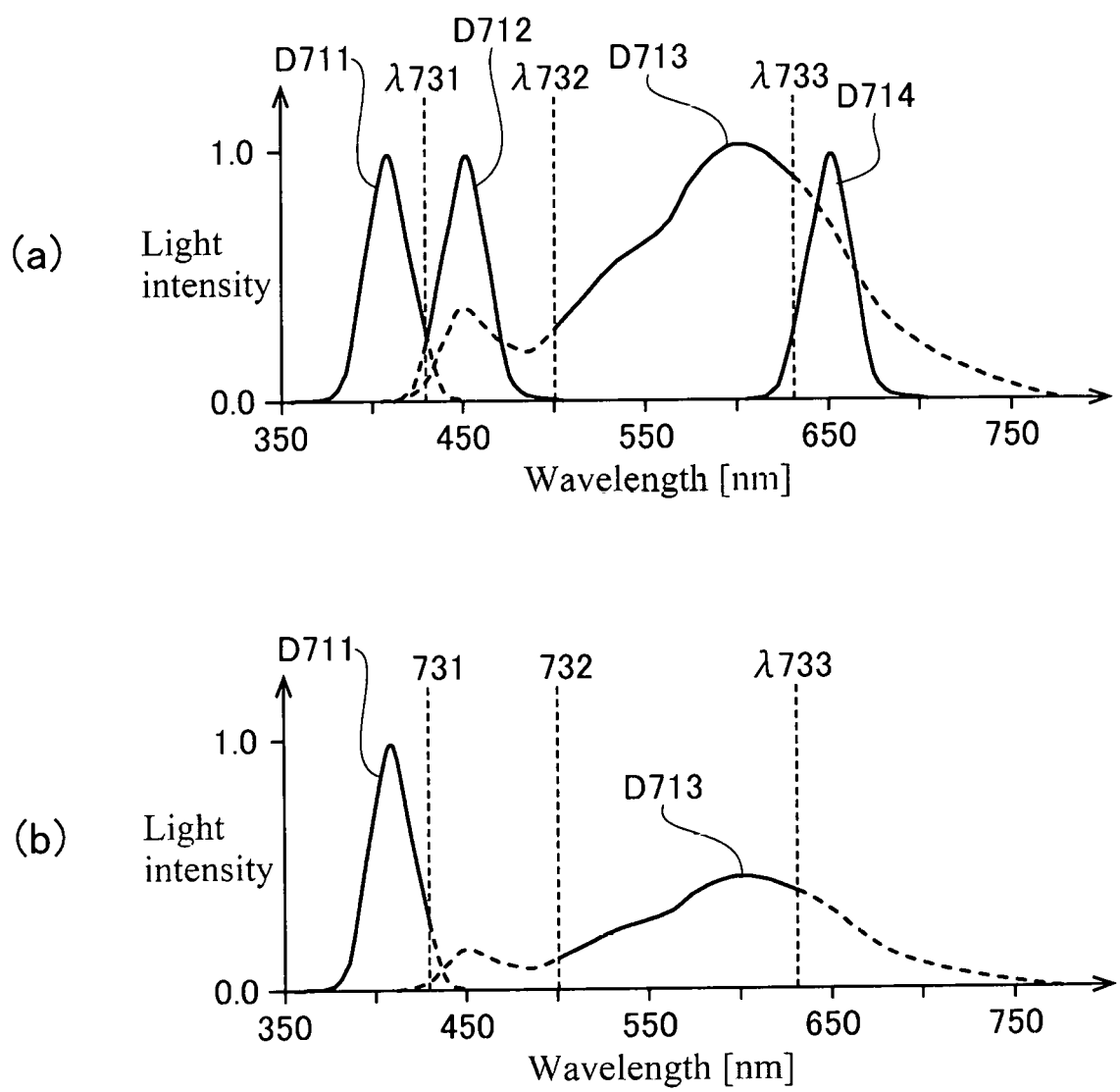
FIG. 16 is a diagram showing a spectral intensity distribution of irradiation light emitted from the endoscope light source device according to the seventh embodiment of the present disclosure.

FIG. 16 shows the spectral intensity distributions of the irradiation light L emitted from the light source device 207 in respective observation modes, similarly to FIG. 4.

As shown in FIG. 16, the spectral intensity distributions of irradiation light L in the seventh embodiment are the same as those of the irradiation light L in the third embodiment, with the exception of a spectral intensity distribution D713 of light emitted from the third light source unit 713. It should be noted that the cutoff wavelengths λ731 to λ733 of the dichroic mirrors 731 to 733 of the seventh embodiment are different from λ331 to λ333 of the dichroic mirrors 331 to 333 of the third embodiment. For this reason, the spectral intensity distributions of light emitted as the irradiation light L (the regions shown by solid lines in the spectral intensity distribution shown in FIG. 16) are different from the spectral intensity distributions of the irradiation light L in the third embodiment.

Unlike the light source device 203 of the third embodiment, the light source device 207 of the seventh embodiment uses a fluorescent LED (third light source unit 713) instead of a green LED (third light source unit 313), and therefore the spectral intensity distribution of the irradiation light L (normal light) closely approaches a flat distribution in the visible range. Accordingly, the subject can be irradiated with irradiation light L (normal light) that is close to natural white light.

Also, although the third light source unit 713 has a yellow phosphor, the present disclosure is not limited to this. For example, instead of a yellow phosphor, the third light source unit 713 may have a green phosphor that has a peak wavelength around 550 nm and a red phosphor that has a peak wavelength around 650 nm. Alternatively, the third light source unit 713 may have a yellow phosphor that is intense in a wider wavelength band than that shown in FIG. 16.

Illustrative embodiments of the present disclosure have been described above. The embodiments of the present disclosure are not limited to the embodiments described above, and various changes can be made without departing from the scope of the technical idea of the present disclosure. For example, appropriate combinations of embodiments and the like explicitly given as examples in this specification and obvious embodiments and the like are also encompassed in embodiments of the present disclosure. For example, LEDs are envisioned as the solid-state light emitting elements in the above embodiments. The present disclosure is not limited to this, and LDs (Laser Diodes) can also be employed as the solid-state light emitting elements.

Figure 17:
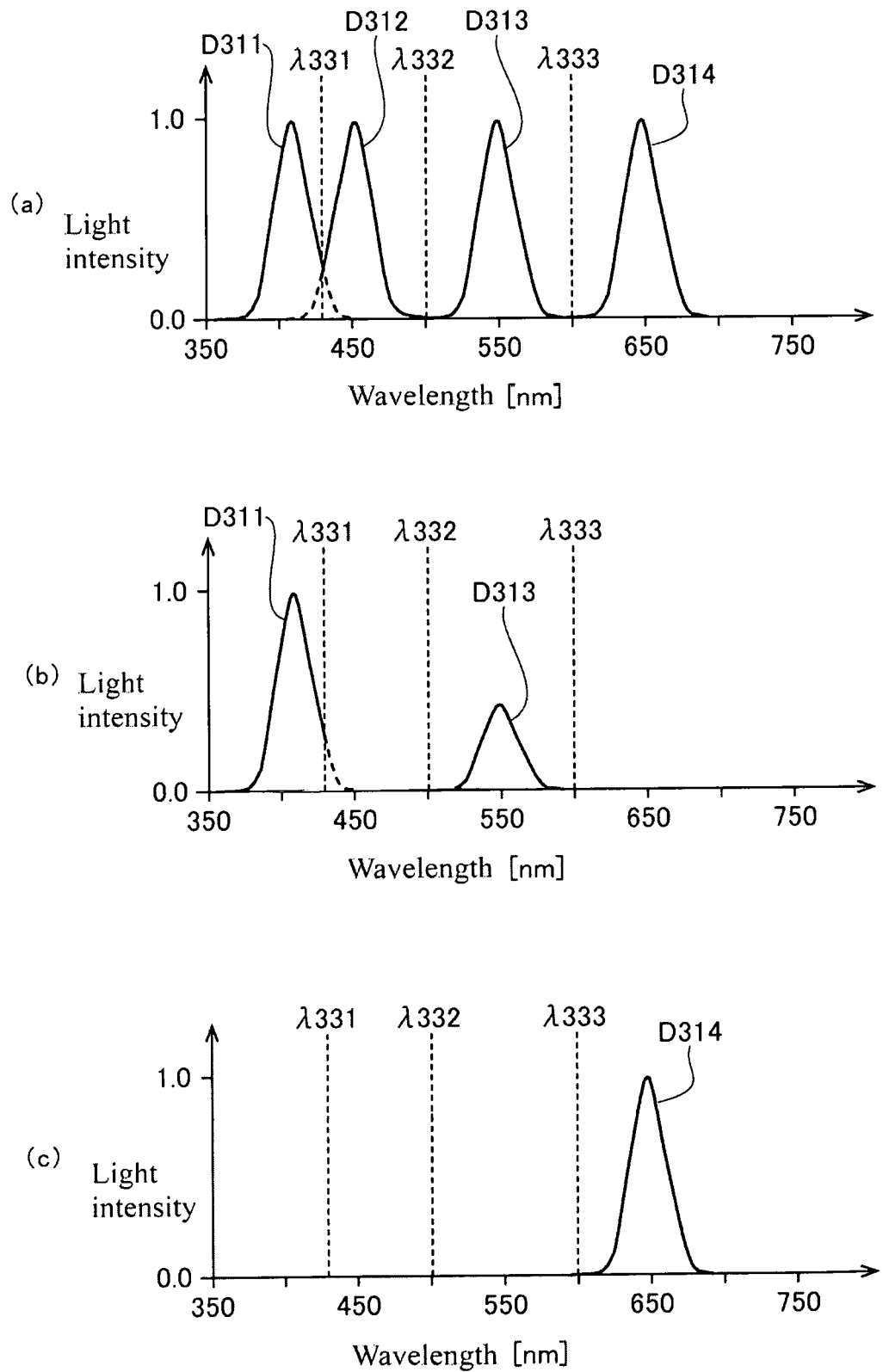
FIG. 17 is a diagram showing a spectral intensity distribution of irradiation light emitted from an endoscope light source device according to a variation of the third embodiment of the present disclosure.

FIG. 17 shows the spectral intensity distributions of the irradiation light L emitted from the light source device 203 in a variation of the third embodiment. In the present variation, there are three observation modes (the normal observation mode, a first special observation mode, and a second special observation mode). FIG. 17(a) shows the spectral intensity distribution of the irradiation light L (normal light) in the normal observation mode, FIG. 17(b) shows the spectral intensity distribution of the irradiation light L (special light) in the first special observation mode, and FIG. 17(c) shows the spectral intensity distribution of the irradiation light L (special light) in the second special observation mode. In FIG. 17, the horizontal axis in the spectral intensity distributions indicates the wavelength (nm), and the vertical axis indicates the intensity of the irradiation light L. Note that the vertical axis is standardized such that the maximum intensity value is 1.

The operations in the normal observation mode are the same as in the third embodiment, which were described using FIGS. 7 and 8. Accordingly, in the normal observation mode, irradiation light L (normal light) having the same spectral characteristics as in FIG. 8(a) is emitted. Irradiating the subject with this irradiation light L (normal light) makes it possible to obtain a normal color captured image.

The operations in the first special observation mode are the same as those in the special observation mode in the third embodiment, which were described using FIGS. 7 and 8. Accordingly, in the first special observation mode, irradiation light L (special light) having the same spectral characteristics as in FIG. 8(b) is emitted. It is therefore possible to obtain a captured image in which mainly outer-layer blood vessels are emphasized.

When the electronic endoscope system 1 is in the second special observation mode, the fourth light source unit 314 is driven to emit light, and the first to third light source units 311 to 313 are not driven to emit light. Accordingly, in the irradiation light L (special light), the percentage of light at the wavelength of approximately 650 nm, which is the peak of the light absorption rate of hemoglobin, is relatively higher (i.e., the light is narrow band light having a peak at only a wavelength of approximately 650 nm), and it is possible to obtain a captured image in which mainly deep-layer blood vessels are emphasized.

The invention claimed is:

1. An endoscope light source device comprising:
   a first light source unit that emits light in a first wavelength band, with a peak wavelength of approximately 415 nm;
   a second light source unit that emits light in a second wavelength band having a peak wavelength of approximately 550 nm;
   a first dichroic mirror configured to combine a light path of the light emitted from the first light source unit and a light path of the light emitted from the second light source unit; and
   light source drive circuitry configured to control light emission of the first light source unit and the second light source unit separately in accordance with a plurality of modes,
   wherein when the first light source unit and the second light source unit are driven by the light source drive circuitry to emit light in a first mode, the light in the first wavelength band and the light in the second wavelength band are emitted at a first intensity ratio and combined by the first dichroic mirror to obtain normal light that has a wide wavelength range in a visible light region, and the normal light is supplied to an endoscope, and
   when the first light source unit and the second light source unit are driven by the light source drive circuitry to emit light in a second mode, the light in the first wavelength band and the light in the second wavelength band are emitted at a second intensity ratio having a relatively lower ratio of the light in the second wavelength band than the first intensity ratio, and are combined by the first dichroic mirror to obtain special light that has a high light absorption rate in a specific biological tissue, and the special light is supplied to the endoscope.

2. The endoscope light source device according to claim 1, further comprising:
   a third light source unit that emits light in a third wavelength band having a peak wavelength that is different from the peak wavelength of the first wavelength band and the peak wavelength of the second wavelength band; and
   a second dichroic mirror configured to combine a light path of light combined by the first dichroic mirror and a light path of the light emitted from the third light source unit,
   wherein in the first mode, the light source drive circuitry causes the third light source unit to emit light at a predetermined intensity ratio with respect to the first light source unit and the second light source unit, and
   in the second mode, the light source drive circuitry does not cause the third light source unit to emit light.

3. The endoscope light source device according to claim 2, further comprising:
   a fourth light source unit that emits light in a fourth wavelength band having a peak wavelength that is different from the peak wavelength of the first wavelength band, the peak wavelength of the second wavelength band, and the peak wavelength of the third wavelength band; and
   a third dichroic mirror configured to combine a light path of light combined by the second dichroic mirror and a light path of the light emitted from the fourth light source unit, wherein in the first mode, the light source drive circuitry causes the fourth light source unit to emit light at a predetermined intensity ratio with respect to the first light source unit, the second light source unit, and the third light source unit, and
in the second mode, the light source drive circuitry does not cause the fourth light source unit to emit light.

4. The endoscope light source device according to claim 1,
wherein the first light source unit has
a first solid-state light emitting element, and
a first phosphor that is excited by light emitted from the first solid-state light emitting element and emits light.

5. The endoscope light source device according to claim 4,
wherein the first solid-state light emitting element emits light in a purple wavelength band,
the first phosphor is a phosphor that emits fluorescent light in a blue wavelength band, and
in the light emitted from the first light source unit, an intensity of the fluorescent light in the blue wavelength band is weaker than an intensity of the light in the purple wavelength band.

6. The endoscope light source device according to claim 1,
wherein the second light source unit has
a second solid-state light emitting element, and
a second phosphor that is excited by light emitted from the second solid-state light emitting element and emits light.

7. The endoscope light source device according to claim 6,
wherein the second phosphor includes two phosphors that are excited by the light emitted from the second solid-state light emitting element and emit light having mutually different peak wavelengths.

8. An endoscope system comprising:
the endoscope light source device according to claim 1; and
an endoscope.

9. An apparatus comprising:
a first light source unit that emits light in a first wavelength band having a peak wavelength;
a second light source unit that emits light in a second wavelength band having a peak wavelength that is different from a peak wavelength of the first wavelength band;
a third light source unit that emits light in a third wavelength band having a peak wavelength of approximately 650 nm that is different from the peak wavelength of the first wavelength band and the peak wavelength of the second wavelength band;
a first dichroic mirror for combining a light path of the light emitted from the first light source unit and a light path of the light emitted from the second light source unit;
a second dichroic mirror configured to combine a light path of light combined by the first dichroic mirror and a light path of the light emitted from the third light source unit; and
light source drive circuitry configured to control light emission of the first light source unit and the second light source unit separately in accordance with a plurality of modes,
wherein when the first light source unit, the second light source unit, and the third light source unit are driven by the light source drive circuitry to emit light in a first mode, the light in the first wavelength band, the light in the second wavelength band, and the light in the third wavelength band are emitted at a first intensity ratio and combined by the first dichroic mirror and the second dichroic mirror to obtain normal light that has a wide wavelength range in a visible light region and a peak wavelength of approximately 650 nm, and the normal light is supplied to an endoscope, and
when the first light source unit and the second light source unit are driven by the light source drive circuitry to emit light in a second mode, the light in the first wavelength band and the light in the second wavelength band are emitted at a second intensity ratio having a relatively lower ratio of the light in the second wavelength band than the first intensity ratio, and are combined by the first dichroic mirror to obtain special light that has a high light absorption rate in a specific biological tissue, and the special light is supplied to the endoscope.

10. The apparatus according to claim 9, wherein in the first mode, the light source drive circuitry causes the third light source unit to emit light at a predetermined intensity ratio with respect to the first light source unit and the second light source unit, and
in the second mode, the light source drive circuitry does not cause the third light source unit to emit light.

11. The apparatus according to claim 10, further comprising:
a fourth light source unit that emits light in a fourth wavelength band having a peak wavelength that is different from the peak wavelength of the first wavelength band, the peak wavelength of the second wavelength band, and the peak wavelength of the third wavelength band; and
a third dichroic mirror for combining a light path of light combined by the second dichroic mirror and a light path of the light emitted from the fourth light source unit,
wherein in the first mode, the light source drive circuitry causes the fourth light source unit to emit light at a predetermined intensity ratio with respect to the first light source unit, the second light source unit, and the third light source unit, and
in the second mode, the light source drive circuitry does not cause the fourth light source unit to emit light.

12. The apparatus according to claim 9,
wherein the first light source unit has
a first solid-state light emitting element, and
a first phosphor that is excited by light emitted from the first solid-state light emitting element and emits light.

13. The apparatus according to claim 12,
wherein the first solid-state light emitting element emits light in a purple wavelength band,
the first phosphor is a phosphor that emits fluorescent light in a blue wavelength band, and
in the light emitted from the first light source unit, an intensity of the fluorescent light in the blue wavelength band is weaker than an intensity of the light in the purple wavelength band.

14. The apparatus according to claim 9,
wherein the second light source unit has
a second solid-state light emitting element, and
a second phosphor that is excited by light emitted from the second solid-state light emitting element and emits light.

15. The apparatus according to claim 14,
wherein the second phosphor includes two phosphors that are excited by the light emitted from the second solid-state light emitting element and emit light having mutually different peak wavelengths.

16. The apparatus according to claim 9, wherein the apparatus is an endoscope.

17. The apparatus according to claim 9, wherein the apparatus is an endoscope light source device.

18. A method comprising:
emitting, from a first light source unit, light in a first wavelength band having a peak wavelength;
emitting, from a second light source unit, light in a second wavelength band having a peak wavelength that is different from a peak wavelength of the first wavelength band;
emitting, from a third light source unit, light in a third wavelength band having a peak wavelength of approximately 650 nm that is different from the peak wavelength of the first wavelength band and the peak wavelength of the second wavelength band;
combining a light path of the light emitted from the first light source unit and a light path of the light emitted from the second light source unit;
combining a light path of light combined by a first dichroic mirror and a light path of the light emitted from the third light source unit; and
controlling light emission of the first light source unit and the second light source unit separately in accordance with a plurality of modes,
wherein, when the first light source unit, the second light source unit, and the third light source unit are controlled to emit light in a first mode, the light in the first wavelength band, the light in the second wavelength band, and the light in the third wavelength band are emitted at a first intensity ratio and combined to obtain normal light that has a wide wavelength range in a visible light region and a peak wavelength of approximately 650 nm, and the normal light is supplied to an endoscope, and
wherein, when the first light source unit and the second light source unit are driven by a light source drive circuit to emit light in a second mode, the light in the first wavelength band and the light in the second wavelength band are emitted at a second intensity ratio having a relatively lower ratio of the light in the second wavelength band than the first intensity ratio and combined to obtain special light that has a high light absorption rate in a specific biological tissue, and the special light is supplied to the endoscope.

19. The method according to claim 18, further comprising:
wherein, in the first mode, the third light source unit is controlled to emit light at a predetermined intensity ratio with respect to the first light source unit and the second light source unit, and
wherein, in the second mode, the third light source unit is controlled to not emit light.

20. The method according to claim 18, wherein the peak wavelength of the second wavelength band is approximately 550 nm.

* * * * *

UNITED STATES PATENT AND TRADEMARK OFFICE
CERTIFICATE OF CORRECTION

PATENT NO. : 10,610,091 B2
APPLICATION NO. : 15/999500
DATED : April 7, 2020
INVENTOR(S) : Kunihiko Onobori and Masaaki Fukuda It is certified that error appears in the above-identified patent and that said Letters Patent is hereby corrected as shown below:

On the Title Page

Item (56) References Cited, subsection FOREIGN PATENT DOCUMENTS:
Please replace "JP 2012170488 A 10/2012" with --JP 2012170488 A 09/2012--

Signed and Sealed this
First Day of September, 2020

Andrei Iancu
*Director of the United States Patent and Trademark Office*